(12) United States Patent
Gitai et al.

(10) Patent No.: US 7,855,228 B2
(45) Date of Patent: Dec. 21, 2010

(54) ANTIBIOTICS TARGETING MREB

(75) Inventors: Zemer Gitai, San Mateo, CA (US);
Lucy Shapiro, Stanford, CA (US);
Masaaki Wachi, Midori-ku (JP);
Noritaka Iwai, Midori-ku (JP)

(73) Assignees: The Board of Trustees of the Leland Stamford Junior University, Palo Alto, CA (US); Tokyo Institute of Technology, Tokyo (JP)

( * ) Notice: Subject to any disclaimer, the term of this patent is extended or adjusted under 35 U.S.C. 154(b) by 774 days.

(21) Appl. No.: 11/350,966

(22) Filed: Feb. 8, 2006

(65) Prior Publication Data

US 2006/0241185 A1     Oct. 26, 2006

Related U.S. Application Data

(60) Provisional application No. 60/652,084, filed on Feb. 10, 2005.

(51) Int. Cl.
*C07C 335/32* (2006.01)
*A61K 31/215* (2006.01)
(52) U.S. Cl. ............................... 514/508; 558/4; 558/5
(58) Field of Classification Search ............ 558/4, 558/5; 514/508
See application file for complete search history.

(56) References Cited

U.S. PATENT DOCUMENTS 2,680,745 A  *  6/1954  Craig et al. .............. 548/325.1

OTHER PUBLICATIONS

Tarasiuk et al., Chem. Abst. 123:285414 (1995).*
El-Hewehi et al., Chem. Abst. 58:20495 (1963).*
Tait et al. Chem. Abstr. 114:98016 (1991).*
Liebscher et al., Chem. Abst. 104:68783 (1986).*
Liebscher et al., Chem. Abst. 104:109621 (1986).*
Defeu Soufo, H.J., et al., "Actin-like proteins MreB and Mbl from *Bacillus subtilis* are required for bipolar positioning of replication origins," (2003) *Current Biology*, 13:1916-1920.
Defeu Soufo, H.J., et al., "Dynamic movement of actin-like proteins within bacterial cells," (2004) *EMBO Reports*, 5(8):789-794.
Figge, R.M., et al., "MreB, the cell shape-determining bacterial actin homologue, co-ordinates cell wall morphogenesis in *Caulobacter crescentus*," (2004) *Molecular Microbiology*, 51(5):1321-1332.

Gitai, Z, et al., "An actin-like gene can determine cell polarity in bacteria," (2004) *PNAS*, 101(23):8643-8648.
Holtzendorff, J., et al., "Oscillating global regulators control the genetic circuit driving a bacterial cell cycle," (2004) *Science* 304:983-987.
Iwai, N., et al., "Novel S-Benzylisothiourea compound that induces spherical cells in *Escherichia coli* probably by acting on a rod-shape-determining protein(s) other than penicillin-binding protein 2," *Bioscience Biotechnology Biochemistry* 66(12):2658-2662.
Jensen, R., et al., "Dynamic localization of proteins and DNA during a bacterial cell cycle," (2002) *Nature Reviews*, 3:167-175.
Kruse, T., et al., "Dysfunctional MreB inhibits chromosome segregaton in *Escherichia coli*," (2003) *The EMBO Journal*, 22:5283-5292.
Marczynski, G.T., et al., "Cell-cycle control of a cloned chromosomal origin of replication from *Caulobacter crescentus*," (1992) *Journal of Molecular Biology*, 226:959-977.
Marczynski, G.T., et al., "Control of chromosome replication in *Caulobacter crescentus*," (2002) *Annual Review of Microbiology*, 56:625-656.
Viollier, P.H., et al., "A dynamically localized histidine kinase controls the asymmetric distribution of polar pili proteins," (2002) *The EMBO Journal*, 21(17):4420-4428.
Viollier, P.H., et al., "Rapid and sequential movement of individual chromosomal loci to specific subcellular locations during bacterial DNA replication," (2004) *PNAS*, 101(25):9257-9262.
Winzeler, E., et al., "Use of flow cytometry to identify a *Caulobacter* 4.5 S RNA temperature-sensitive mutant defective in the cell cycle," (1995) *Journal of Molecular Biology*, 251:345-365.
Database CAPLUS on STN Chemical abstracts, (Tarasiuk et al.) 'Synthesis, structure and physicochemical and biological properties of selected S-(arylalkyl)isothiouronium 2-(aryloxy)propionates', 1995, 123:285414, 4 pgs.
Database CAPLUS on STN Chemical abstracts, (El-Hewehi, Z.) 'Reaction products of chlorinated benzyl chloride and their applicability as pestcontrolling agents', 1962, 58:20495, 5 pgs.

* cited by examiner

*Primary Examiner*—Peter G O'Sullivan
(74) *Attorney, Agent, or Firm*—Bozicevic, Field & Francis LLP; Pamela J. Sherwood

(57) ABSTRACT

The identification of MreB as essential for bacterial chromosome segregation provides a new target for antibiotic action. The MreB function is useful in the development of screening assays for new antibiotics, which may use, for example, genetic mutants in MreB, tests of MreB mediated chromosome segregation, and the like. In one embodiment of the invention, the antibiotic is an isothiourea compound, which may comprise a polyhalogenated benzyl group, e.g. at the 4 position, the 2,4 position, etc. A pharmaceutical composition comprising an MreB targeted antibiotic as an active agent is administered to a patient suffering from a microbial infection, particularly bacterial infections.

1 Claim, 12 Drawing Sheets

```
                         SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: synthetic primer

<400> SEQUENCE: 1
atgggagtgt gcttgtcgac tcgcc                                           25

<210> SEQ ID NO 2
<211> LENGTH: 25
<212> TYPE: DNA
<213> ORGANISM: Artificial Sequence
<220> FEATURE:
<223> OTHER INFORMATION: synthetic primer

<400> SEQUENCE: 2
accaggcagg gtcgacagac acttc                                           25

<210> SEQ ID NO 3
<211> LENGTH: 25
<212> TYPE: DNA
<213> ORGANISM: Artificial Sequence
<220> FEATURE:
<223> OTHER INFORMATION: synthetic primer

<400> SEQUENCE: 3
ggagaaccgg aagcttaata cagag                                           25

<210> SEQ ID NO 4
<211> LENGTH: 25
<212> TYPE: DNA
<213> ORGANISM: Artificial Sequence
<220> FEATURE:
<223> OTHER INFORMATION: synthetic primer

<400> SEQUENCE: 4
tttagcatgc ctggtctgat acgag                                           25

<210> SEQ ID NO 5
<211> LENGTH: 25
<212> TYPE: DNA
<213> ORGANISM: Artificial Sequence
<220> FEATURE:
<223> OTHER INFORMATION: synthetic primer

<400> SEQUENCE: 5
atgggagtgt gcttctagac tcgcc                                           25

<210> SEQ ID NO 6
<211> LENGTH: 25
<212> TYPE: DNA
<213> ORGANISM: Artificial Sequence
<220> FEATURE:
<223> OTHER INFORMATION: synthetic primer
```

```
<400> SEQUENCE: 6
tgcctgcatc gctagcctct tcgct                                          25

<210> SEQ ID NO 7
<211> LENGTH: 29
<212> TYPE: DNA
<213> ORGANISM: Artificial Sequence
<220> FEATURE:
<223> OTHER INFORMATION: synthetic primer

<400> SEQUENCE: 7
ggagaaaccg cgcgacgcag agcatgcgg                                      29

<210> SEQ ID NO 8
<211> LENGTH: 28
<212> TYPE: DNA
<213> ORGANISM: Artificial Sequence
<220> FEATURE:
<223> OTHER INFORMATION: synthetic primer

<400> SEQUENCE: 8
ggcttctacc gcatgccagt cgcggatt                                       28
```

ANTIBIOTICS TARGETING MREB

This invention was made with Government support under contract R01GM51426 awarded by the National Institutes of Health. The Government has certain rights in this invention.

BACKGROUND OF THE INVENTION

The emergence of multi-drug-resistant pathogens has become a serious problem in the chemotherapy of bacterial infectious diseases. One of the strategies that can be used to overcome this problem is to find new bacterial protein targets that provide functions essential for cell growth or replication; and to screen for agents that disrupt in some way that essential function.

The process of DNA replication and cell division is potentially an attractive target for antibiotic action. To maintain a consistent number of chromosomes, cells must ensure that during cell division the chromosome is reproducibly replicated, and that each of the new chromosomes is segregated to one of the two daughter cells. Although the ability of bacteria to faithfully replicate and segregate their chromosomes has been appreciated for over forty years, the molecular mechanism by which bacteria execute the segregation process has remained elusive.

Observing the placement and movement of chromosomal loci has revealed that all bacteria examined have highly reproducible, ordered chromosomal structure, with loci exhibiting a linear correlation between their genetic location on the chromosome and their placement along the long axis of the cell. Nonetheless, the details of chromosomal topology vary among species. For example, the rod-shaped bacteria *E. coli* and *B. subtilis* localize their origins of replication to the mid-cell and quarter-cell positions at different stages of the cell cycle, whereas in the crescent-shaped *Caulobacter crescentus* chromosomal origins are at the cell poles. Direct examination of chromosome segregation in live cells revealed that the origin region (defined as the site of the initiation of DNA replication) is the first region of the chromosome to be segregated in all species examined.

The rapid, directed movement of the origins excludes the cell growth-related mechanisms initially proposed for chromosome segregation and is suggestive of an active mechanism for origin transport. Several candidates have been put forth as potential contributors to the force that separates the chromosomes. The coincident timing of DNA replication and segregation suggests that these processes are coupled and that the act of DNA replication could provide the motive force for chromosome segregation. The observation that the DNA replication machinery is stationary in *B. subtilis* and *E. coli* led to the refinement of such models into the "extrusion-capture" model, wherein the extrusion of DNA from an immobile replisome forces it poleward, where it is then captured by as-yet unidentified factors. Coordinate transcription of origin-proximal reading frames oriented away from the origin has also been proposed to contribute to the movement of bacterial chromosomes. Though these models are compelling and elegant, they lack experimental validation.

In contrast, the mechanisms directing eukaryotic chromosome segregation are well characterized. Eukaryotes use a microtubule-based cytoskeletal system for chromosome partitioning. After replication, chromosome sisters are paired, and microtubules are attached to specific, centromeric chromosomal loci through a kinetochore protein complex. Once attached, the microtubules direct chromosome migration to opposite poles through dynamic polymerization cycles and the action of motor proteins. Bacterial proteins that could provide a function analogous to the kinetochore protein complex would be an attractive target for antibiotic action.

There is a clinical need for novel antibiotic agents. The present invention addresses this need.

Selected Literature Citations

Defeu Soufo and Graumann (2004). Dynamic movement of actin-like proteins within bacterial cells. EMBO Rep. 5, 789-794. Ely (1991). An actin-like gene can determine cell polarity in bacteria. Proc. Natl. Acad. Sci. USA 101, 8643-8648. Holtzendorff et al. (2004). Oscillating global regulators control the genetic circuit driving a bacterial cell cycle. Science 304, 983-987.

Iwai et al. (2002). Novel S-benzylisothiourea compound that induces spherical cells in *Escherichia coli* probably by acting on a rod-shape-determining protein(s) other than penicillin-binding protein 2. Biosci. Biotechnol. Biochem. 66, 2658-2662.

Jensen et al. (2002). Dynamic localization of proteins and DNA during a bacterial cell cycle. Nat. Rev. Mol. Cell Biol. 3, 167-176. Kruse et al. (2003). Dysfunctional MreB inhibits chromosome segregation in *Escherichia coli*. EMBO J. 22, 5283-5292. Soufo and Graumann (2003). Actin-like proteins MreB and Mbl from *Bacillus subtilis* are required for bipolar positioning of replication origins. Curr. Biol. 13, 1916-1920.

Marczynski and Shapiro (1992). Cell-cycle control of a cloned chromosomal origin of replication from *Caulobacter crescentus*. J. Mol. Biol. 226, 959-977. Winzeler and Shapiro (1995). Use of flow cytometry to identify a *Caulobacter* 4.5 S RNA temperature-sensitive mutant defective in the cell cycle. J. Mol. Biol. 251, 346-365. Marczynski and Shapiro (2002). Control of chromosome replication in *Caulobacter crescentus*. Annu. Rev. Microbiol. 56, 625-656. Figge et al. (2004). MreB, the cell shape-determining bacterial actin homologue, coordinates cell wall morphogenesis in *Caulobacter crescentus*. Mol. Microbiol. 51, 1321-1332.

Viollier et al. (2002). A dynamically localized histidine kinase controls the asymmetric distribution of polar pili proteins. EMBO J. 21, 4420-4428. Viollier et al. (2004). Rapid and sequential movement of individual chromosomal loci to specific subcellular locations during bacterial DNA replication. Proc. Natl. Acad. Sci. USA 101, 9257-9262.

SUMMARY OF THE INVENTION

Methods and compositions are provided for the use of antibiotics targeted to the bacterial protein MreB. In one embodiment of the invention, the antibiotic is an isothiourea compound, which may comprise a polyhalogenated benzyl group, e.g. at the 4 position, the 2,4 position, etc. A pharmaceutical composition comprising an MreB targeted antibiotic as an active agent is administered to a patient suffering from a microbial infection, particularly bacterial infections. The compounds are also effective at killing a variety of microbial organisms in vitro. An MreB targeted antibiotic may be administered alone, or in combination with other bacteriocidal agents.

The identification of MreB as essential for bacterial chromosome segregation provides a new target for antibiotic action. The MreB function is useful in the development of screening assays for new antibiotics, which may use, for example, genetic mutants in MreB, tests of MreB mediated chromosome segregation, and the like. MreB is also useful in the modeling of novel antibiotics and cellular interactions therefrom.

DESCRIPTION OF THE SPECIFIC EMBODIMENTS

Figure 1:
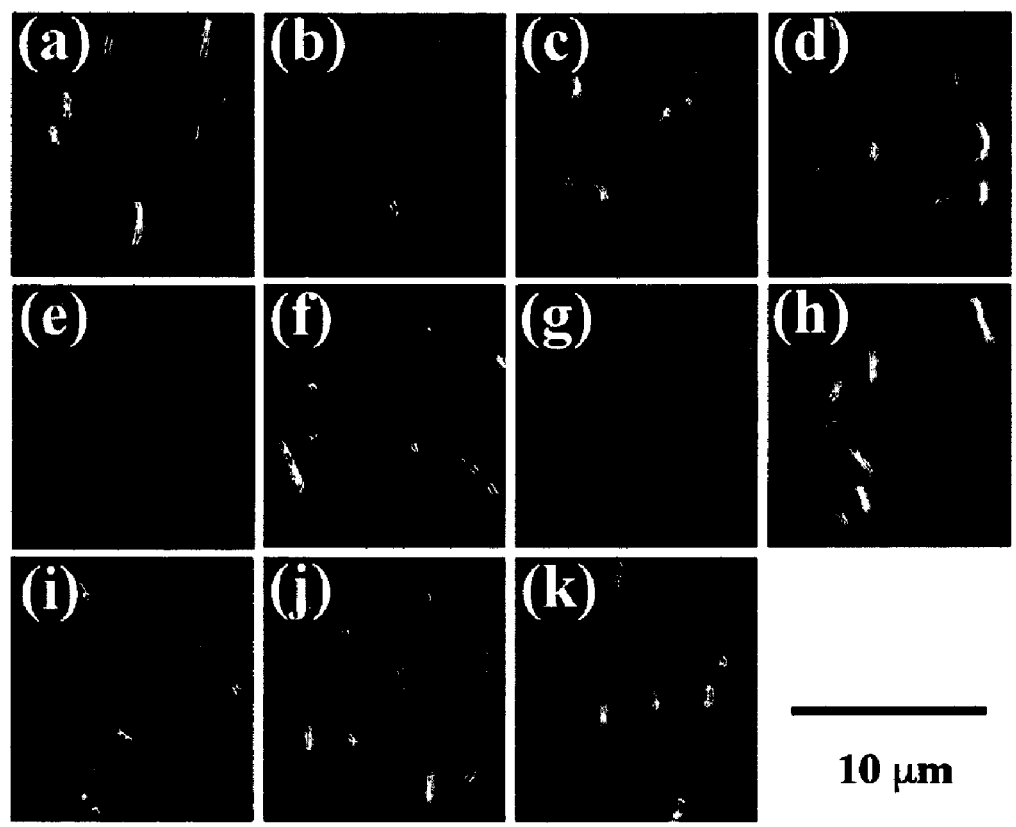
FIG. 1. Effects of S-Benzylisothiurea Derivatives on *E. coli* Cell Shape. Differential interference contrast microphotographs are shown of *E. coli* MG1655 cells after (a) no treatment or treatment with (b) 9.39 µg/ml of 1, (c) 9.39 µg/ml of 2, (d) 300 µg/ml of 3, (e) 300 µg/ml of 4, (f) 300 µg/ml of 5, (g) 300 µg/ml of 6, (h) 300 µg/ml of 7, (i) 150 µg/ml of 8, (j) 300 µg/ml of 9 or (k) 300 µg/ml of 10 for 16 h. Bar: 10 µm.

Compositions and methods are provided for the use of MreB targeted antibiotics as antimicrobial agents. MreB targeted antibiotics may be provided as a pharmaceutical formulation, where the active agent is combined with a pharmaceutically acceptable carrier. The agents are effective at killing a variety of microbial organisms in vitro and in vivo. MreB targeted antibiotic(s) are administered alone or in combination with other active agents to a patient suffering from or predisposed to an infection, in a dose and for a period of time sufficient to reduce the patient population of microbial pathogens, e.g. gram negative bacteria, gram positive bacteria, etc., and are of particular interest for the treatment of gram negative bacteria, such as *Escherichia, Pseudomonas, Salmonella, Chlamydia*, etc. The identification of MreB as a target for antibiotic action provides a basis for further therapeutic development, through screening assays designed to detect molecules that act on this target.

Antibiotics of the present invention delocalize MreB in a bacterial cell. Mutations in MreB provided herein are each sufficient to render cells insensitive to these antibiotics, e.g. to the test agent A22, and no mutations in any other gene have been found to cause resistance. In addition to demonstrating specificity, the resistant mreB alleles shed light on how these antibiotics interact with MreB. The mutated residues are dispersed throughout the protein, but when mapped onto the crystal structure of a close homolog, they all cluster near MreB's nucleotide binding site.

The movement of the origin in chromosome segregation depends on MreB. ChIP assays shown herein demonstrate that MreB biochemically associates either directly or indirectly with chromosomal DNA, and that this association exhibits specificity. The fact that the origin-proximal region both depends on MreB for segregation and binds MreB suggests that this region binds to MreB to mediate its segregation, which in turn promotes the segregation of the rest of the chromosome. In this manner, the origin-proximal DNA functions as a bacterial centromere.

DEFINITIONS

The term "effective amount", or "therapeutically effective amount" as used herein means a dosage sufficient to provide for treatment for the disease state being treated or to otherwise provide the desired effect. The precise dosage will vary according to factors such as subject-dependent variables (e.g., age, immune system health, etc.), the disease (e.g., the species of the infecting pathogen), and the treatment being effected. In the case of a pathogen infection, an "effective amount" is that amount necessary to substantially improve the likelihood of treating the infection, in particular that amount which improves the likelihood of successfully preventing infection or eliminating infection when it has occurred.

By "subject" or "individual" or "patient" or "host" is meant any subject for whom or which therapy is desired. Human subjects are of particular interest. Other subjects may include non-human primates, cattle, sheep, goats, dogs, cats, birds (e.g., chickens or other poultry), guinea pigs, rabbits, rats, mice, horses, and so on.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

MreB Targeted Antibiotic Compositions

For use in the subject methods, any of the provided MreB targeted antibiotics, modifications thereof, or a combination of one or more forms may be used. MreB targeted antibiotics may include compounds of the formula as follows, however the antibiotic and formulations will generally exclude S-(3,4-Dichlorobenzyl)isothiourea.

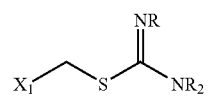

I where each R is independently selected from H, and a linear or branched lower alkyl, such as methyl, ethyl, propyl, isopropyl, butyl, pentyl, and the like; and $X_1$ is a substituted benzyl comprising from one to five substituents, each substituent being independently selected from F, Cl, Br, I, a lower alkyl, $CF_3$, $CCl_3$, $NO_2$, $SO_2$, —OCH$_3$, and SH. One or more of the annular carbons may be optionally substituted with a heteroatom, including N, S, and O.

In one embodiment, the antibiotic has the structure:

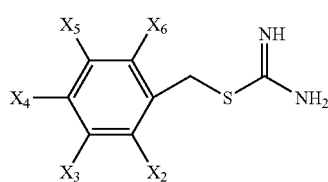

II where each of $X_2$, $X_3$, $X_4$, $X_5$ and $X_6$ is independently selected from H, F, Cl, Br, I, a lower alkyl, CF$_3$, CCl$_3$, NO$_2$, SO$_2$, —OCH$_3$, and SH. Compounds of interest also include derivatives, e.g. at one or more hydroxyl or amino groups. Such derivatives may be ester derivatives, where the attached ester substituents include one or more amino or carboxylate groups.

Compounds of interest include, without limitation, S-(4-Bromo-benzyl)-isothiourea; S-(4-Iodo-benzyl)-isothiourea; S-(4-Chloro-benzyl)-isothiourea; S-(4-Fluoro-benzyl)-isothiourea; S-(4-methyl-benzyl)-isothiourea; S-(4-Trifluoromethyl-benzyl)-isothiourea; S-(4-Nitro-benzyl)-isothiourea; S-(2,4-Dibromo-benzyl)-isothiourea; S-(2,4-Diiodo-benzyl)-isothiourea; S-(2,4-Dichloro-benzyl)-isothiourea; S-(2,4-Difluoro-benzyl)-isothiourea; S-(2,4-Dimethyl-benzyl)-isothiourea; S-(2,4-Ditrifluoromethyl-benzyl)-isothiourea; S-(2,4-Dinitro-benzyl)-isothiourea; and S-(2,4-Dichloro, and 5-fluoro-benzyl)-isothiourea.

Formulations

The antibiotic compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The MreB targeted antibiotics may be systemic after administration or may be localized by the use of an implant or other formulation that acts to retain the active dose at the site of implantation.

In one embodiment, a formulation for topical use comprises a chelating agent that decreases the effective concentration of divalent cations, particularly calcium and magnesium. For example, agents such as citrate, EGTA or EDTA may be included, where citrate is preferred. The concentration of citrate will usually be from about 1 to 10 mM.

The compounds of the present invention can be administered alone, in combination with each other, or they can be used in combination with other known compounds (e.g. anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing MreB targeted antibiotics is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from about 0.1 μg; about 1 μg; about 10 μg; about 0.1 mg; about 1 mg; about 10 mg; to about 100 milligrams per kg weight of subject per administration. A typical dosage may be one tablet taken from one, two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, MreB targeted antibiotics may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; chloramphenicol; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in an MreB targeted antibiotic formulation, e.g. interferon γ, tumor necrosis factor α, interleukin 12, etc.

Kits with unit doses of antibiotic, either in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods of Use

Formulations of MreB targeted antibiotics are administered to a host suffering from or predisposed to a microbial infection. Administration may be topical, localized or systemic, depending on the specific microorganism. Generally the dose of MreB targeted antibiotic will be brought into contact with a microbial population. By contact is meant that the agent and the microorganism are brought within sufficient proximity of one another such that the agent is capable of exerting the desired effect on the microorganism. Contact may be achieved in any convenient manner, such as placing the agent in the same environment as the microorganism, and the like. An effective dose of the antibiotic will decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use.

Microbes of interest include, but are not limited to, Gram-negative bacteria, for example: *Citrobacter* sp.; *Enterobacter* sp.; *Escherichia* sp., e.g. *E. coli*; *Klebsiella* sp.; *Morganella* sp.; *Proteus* sp.; *Providencia* sp.; *Salmonella* sp., e.g. *S. typhi, S. typhimurium*; *Serratia* sp.; *Shigella* sp.; *Pseudomonas* sp., e.g. *P. aeruginosa*; *Yersinia* sp., e.g. *Y. pestis, Y. pseudotuberculosis, Y. enterocolitica*; *Franciscella* sp.; *Pasturella* sp.; *Vibrio* sp., e.g. *V. cholerae, V. parahemolyticus*; *Campylobacter* sp., e.g. *C. jejuni*; *Haemophilus* sp., e.g. *H. influenzae, H. ducreyi*; *Bordetella* sp., e.g. *B. pertussis, B. bronchiseptica, B. parapertussis*; *Brucella* sp., *Neisseria* sp., e.g. *N. gonorrhoeae, N. meningitidis*, etc. Other bacteria of interest include *Legionella* sp., e.g. *L. pneumophila*; *Listeria* sp., e.g. *L. monocytogenes*; *Mycoplasma* sp., e.g. *M. hominis, M. pneumoniae*; *Mycobacterium* sp., e.g. *M. tuberculosis, M. leprae*; *Treponema* sp., e.g. *T. pallidum*; *Borrelia* sp., e.g. *B. burgdorferi*; *Leptospirae* sp.; *Rickettsia* sp., e.g. *R. rickettsii, R. typhi*; *Chlamydia* sp., e.g. *C. trachomatis, C. pneumoniae, C. psittaci*; *Helicobacter* sp., e.g. *H. pylori*, etc.

Various methods for administration may be employed. The antibiotic formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific MreB targeted antibiotic to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously.

MreB targeted antibiotics are also useful for in vitro formulations to kill microbes. For example, MreB targeted antibiotics may be added to animal and/or human food preparations. MreB targeted antibiotics may be included as an additive for in vitro cultures of cells, to prevent the overgrowth of microbes in tissue culture.

The susceptibility of a particular microbe to killing with MreB targeted antibiotics may be determined by in vitro testing, as detailed in the experimental section. Typically a culture of the microbe is combined with MreB targeted antibiotics at varying concentrations for a period of time sufficient to allow the protein to act, usually between about one hour and one day. The viable microbes are then counted, and the level of killing determined.

Compound Screening

The present invention further provides in vitro screening assays to identify agents that modulate an activity of bacterial MreB or other centromere component polypeptides. The screening assays are designed to identify agents that are useful as therapeutic agents for treating bacterial infections. Both cell-based and cell-free assays are provided, as well as in silico rational design screening. Compounds may be screened by the computational modeling of the atomic interactions between drugs and MreB. In one embodiment of the invention, MreB inhibitors are optimized by identification of the atomic interactions between MreB and an inhibitor by in silico docking study.

In some embodiments, the screening assays are cell-free screening assays. In these embodiments, the methods generally involve contacting a bacterial MreB or other centromere component polypeptide with a test agent, and determining the binding, or biological effect, if any, on an activity of the polypeptide, e.g. the ability to bind to a bacterial chromosome, bind nucleotides, form spiral structures, etc. MreB proteins may be obtained from a variety of known polypeptide and polynucleotide sequences among the bacterial species of interest.

In other embodiments, the methods provide cell-based assays. In these embodiments, the methods generally involve contacting a host cell with a candidate agent, and determining the effect, if any, on the polypeptide binding to the chromosome, forming spiral structures, binding nucleotides, and/or to chromosome segregation in the presence and absence of a candidate agent.

A variety of different candidate agents ("test agents") may be screened by the screening methods of the invention. Candidate agents encompass numerous chemical classes, though typically they are organic molecules, and may be small organic compounds having a molecular weight of more than 50 and less than about 2,500 daltons. Candidate agents comprise functional groups necessary for structural interaction with proteins, e.g., hydrogen bonding, and can include at least an amine, carbonyl, hydroxyl or carboxyl group, or at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In some embodiments, the candidate agents have a structure as set forth in Formula I.

Candidate agents, also referred to herein as "test agents") are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents that inhibit the activity or binding of MreB or other components of the bacterial centromere to the desired extent may be selected for further study, and assessed for cellular availability, cytotoxicity, biocompatibility, etc. For example, a candidate agent is assessed for any cytotoxic activity it may exhibit toward a eukaryotic cell, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity toward eukaryotic cells are considered candidate agents for use in therapeutic methods for treating a bacterial infection.

Cell-Free Assays

Cell-free assay methods generally comprise: a) contacting a test agent with a sample containing bacterial MreB or other centromere component polypeptide; and b) assaying an activity of the bacterial polypeptide in the presence of the substance, e.g. DNA binding, chromosome segregation, formation of spiral structures, nucleotide binding, etc. An increase or a decrease in the measured activity in comparison to the activity in a suitable control (e.g., a sample comprising a polypeptide in the absence of the substance being tested) is an indication that the substance modulates an activity of the polypeptide.

An "agent that inhibits an activity of a bacterial MreB or other centromere component polypeptide", as used herein, describes any molecule, e.g. synthetic or natural organic or inorganic compound, protein or pharmaceutical, with the capability of altering an activity of the polypeptide, as described herein. Generally a plurality of assay mixtures is run in parallel with different agent concentrations to obtain a differential response to the various concentrations. Typically one of these concentrations serves as a negative control, i.e. at zero concentration or below the level of detection. The activity can be measured using any assay known in the art.

A variety of other reagents may be included in the screening assay. These include reagents like salts, neutral proteins, e.g. albumin, detergents, etc that are used to facilitate optimal protein-ligand binding and/or reduce non-specific or background interactions. Reagents that improve the efficiency of the assay, such as protease inhibitors, nuclease inhibitors, anti-microbial agents, etc. may be used.

The above screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature, typically between 4° and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the amount of incorporated sulfate will then be detected.

Cell-Based Assays

Cell-based assay generally involve contacting a bacterial cell with a test agent, and determining the effect, if any, on an activity of the peptide. In some embodiments, cells comprising a mutated MreB gene, as described herein, are used. Such mutations include but are not limited to those identified herein, as other genetic variants are readily obtained by screening, e.g. using the methods described herein, or may be synthetically produced. Such mutants are identified as those genetic changes in a bacterial MreB sequence that provide for resistance to an MreB targeted antibiotic, e.g. A22. Mutants can also be generated by recombinant or other methods, e.g. targeting changes to the nucleotide binding site of the protein.

In these embodiments, a mutant bacterial cell comprising a resistant MreB sequence is used. The mutant bacterium serves as a control, and is kept alive by providing necessary nutrients, and the like. A test bacterium comprises a functional copy of MreB. The test bacterium and the control bacterium are individually contacted (e.g., in separate cultures) with a test agent. A test agent that kills the test bacterium, but not the control bacterium, is a candidate anti-bacterial agent. Viability of the bacterium is determined using standard methods, e.g., measuring the optical density of a culture grown in a liquid medium.

In one embodiment, a potential agent for MreB inhibition is selected by performing rational drug design with the three-dimensional coordinates determined for the crystal structures. Preferably the selection is performed in conjunction with computer modeling. Rational design may also be used in conjunction with the genetic modification of MreB peptides by modeling the potential effect of a change in the amino acid sequence.

Computer analysis may be performed with one or more of the computer programs including: GRASP, O (Jones et al. (1991) *Acta Cryst.* A47:110); QUANTA, CHARMM, INSIGHT, SYBYL, MACROMODEL; ICM, and CNS (Brunger et al. (1998) *Acta Cryst.* D54:905). In a further embodiment of this aspect of the invention, an initial drug screening assay is performed using the three-dimensional structure so obtained, preferably along with a docking computer program. Such computer modeling can be performed with one or more Docking programs such as DOC, GRAM and AUTO DOCK. See, for example, Dunbrack et al. (1997) *Folding & Design* 2:27-42.

It should be understood that in the drug screening and protein modification assays provided herein, a number of iterative cycles of any or all of the steps may be performed to optimize the selection. For example, assays and drug screens that monitor bacterial cell growth in the presence and/or absence of a potential inhibitor are also included in the present invention and can be employed as an assay or drug screen, usually as a single step in a multi-step protocol.

The structure of the MreB protein is useful in the design of agents that mimic the activity and/or specificity of the binding interaction. The structures encoded by the data may be computationally evaluated for an ability to associate with chemical entities. This provides insight into an element's ability to associate with chemical entities. Chemical entities that are capable of associating with these domains may alter ATP binding, etc. Such chemical entities are potential drug candidates. Alternatively, the structure encoded by the data may be displayed in a graphical format. This allows visual inspection of the structure, as well as visual inspection of the structure's association with chemical entities.

In one embodiment of the invention, an invention is provided for evaluating the ability of a chemical entity to associate with an MreB protein. This method comprises the steps of employing computational means to perform a fitting operation between the chemical entity and the interacting surface of the polypeptide or nucleic acid; and analyzing the results of the fitting operation to quantify the association. The term "chemical entity", as used herein, refers to chemical compounds, complexes of at least two chemical compounds, and fragments of such compounds or complexes. Molecular design techniques are used to design and select chemical entities, including inhibitory compounds, capable of binding to the protein. Such chemical entities may interact directly with certain key features of the structure.

It will be understood by those skilled in the art that not all of the atoms present in a significant contact residue need be present in a competitive binding agent. In fact, it is only those few atoms that shape the loops and actually form important contacts that are likely to be important for activity. Those skilled in the art will be able to identify these important atoms based on the structure model of the invention, which can be constructed using the structural data herein.

The design of compounds that bind to MreB generally involves consideration of two factors. First, the compound must be capable of either competing for binding with DNA, ATP, etc.; or physically and structurally associating with the MREB domains. Non-covalent molecular interactions important in this association include hydrogen bonding, van der Waals interactions, hydrophobic interactions and electrostatic interactions.

The compound must be able to assume a conformation that allows it to interact with the binding pocket. Although certain portions of the compound will not directly participate in these associations, those portions may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several interacting chemical moieties.

Computer-based methods of analysis fall into two broad classes: database methods and de novo design methods. In database methods the compound of interest is compared to all compounds present in a database of chemical structures and compounds whose structure is in some way similar to the compound of interest are identified. The structures in the database are based on either experimental data, generated by NMR or x-ray crystallography, or modeled three-dimensional structures based on two-dimensional data. In de novo design methods, models of compounds whose structure is in some way similar to the compound of interest are generated by a computer program using information derived from known structures, e.g. data generated by x-ray crystallography and/or theoretical rules. Such design methods can build a compound having a desired structure in either an atom-by-atom manner or by assembling stored small molecular fragments. Selected fragments or chemical entities may then be positioned in a variety of orientations, or docked, within the interacting surface of the RNA. Docking may be accomplished using software such as Quanta (Molecular Simulations, San Diego, Calif.) and Sybyl, followed by energy minimization and molecular dynamics with standard molecular mechanics force fields, such as CHARMM and AMBER.

Specialized computer programs may also assist in the process of selecting fragments or chemical entities. These include: SmoG, GRID (Goodford (1985) J. Med. Chem., 28, pp. 849-857; Oxford University, Oxford, UK; MCSS (Miranker et al. (1991) Proteins: Structure, Function and Genetics, 11, pp. 29-34; Molecular Simulations, San Diego, Calif.); AUTODOCK (Goodsell et al., (1990) Proteins: Structure, Function, and Genetics, 8, pp. 195-202; Scripps Research Institute, La Jolla, Calif.); and DOCK (Kuntz et al. (1982) J. Mol. Biol., 161:269-288; University of California, San Francisco, Calif.)

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates. Useful programs to aid one of skill in the art in connecting the individual chemical entities or fragments include: CAVEAT (Bartlett et al. (1989) In Molecular Recognition in Chemical and Biological Problems", Special Pub., Royal Chem. Soc., 78, pp. 182-196; University of California, Berkeley, Calif.); 3D Database systems such as MACCS-3D (MDL Information Systems, San Leandro, Calif.; and HOOK (available from Molecular Simulations, San Diego, Calif.).

Other molecular modeling techniques may also be employed in accordance with this invention. See, e.g., N. C. Cohen et al., "Molecular Modeling Software and Methods for Medicinal Chemistry, J. Med. Chem., 33, pp. 883-894 (1990). See also, M. A. Navia et al., "The Use of Structural Information in Drug Design", Current Opinions in Structural Biology, 2, pp. 202-210 (1992).

Once the binding entity has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit by the same computer methods described above.

Another approach made possible and enabled by this invention, is the computational screening of small molecule databases. In this screening, the quality of fit of such entities to the binding site may be judged either by shape complementarity or by estimated interaction energy. Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side effects due to unwanted interactions with other proteins.

Compounds of interest can be systematically modified by computer modeling programs until one or more promising potential analogs are identified. In addition systematic modification of selected analogs can then be systematically modified by computer modeling programs until one or more potential analogs are identified. Alternatively a potential modulator could be obtained by initially screening a random peptide library, for example one produced by recombinant bacteriophage. A peptide selected in this manner would then be systematically modified by computer modeling programs as described above, and then treated analogously to a structural analog.

Once a potential modulator/inhibitor is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. The de novo synthesis of one or even a relatively small group of specific compounds is reasonable in the art of drug design.

The success of both database and de novo methods in identifying compounds with activities similar to the compound of interest depends on the identification of the functionally relevant portion of the compound of interest. For drugs, the functionally relevant portion may be referred to as a pharmacophore, i.e. an arrangement of structural features and functional groups important for biological activity. Not all identified compounds having the desired pharmacophore will act as a modulator of inflammation. The actual activity can be finally determined only by measuring the activity of the compound in relevant biological assays. However, the methods of the invention are extremely valuable because they can be used to greatly reduce the number of compounds that must be tested to identify an actual inhibitor.

In order to determine the biological activity of a candidate pharmacophore it is preferable to measure biological activity at several concentrations of candidate compound. The activity at a given concentration of candidate compound can be tested in a number of ways.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Structure-Activity Relationship of S-Benzylisothiourea Derivatives to Induce Spherical Cells in *Escherichia coli*

A22 induces spherical cells and spherical anucleate cells in *E. coli*. The spherical cells induced by the treatment with A22 varied in size, and anucleate cells seemed to be more frequent among the smaller cells. These results suggest that loss of the rod shape in *E. coli* led to asymmetric cell division that resulted in the production of anucleate cells. The β-lactam antibiotic, mecillinam, is also known to induce spherical cells by inhibiting the penicillin-binding protein (PBP) 2 that is involved in side-wall peptidoglycan synthesis. However, an in vitro assay of $^{14}$C-penicillin G binding has suggested that the target molecule of A22 was not PBP 2. A22 may act on a rod-shape-determining protein(s) other than PBP 2 such as RodA or MreB. Thus, A22 is expected to be a novel bioprobe for analyzing the shape-determination mechanism of *E. coli* as well as to be a lead compound for developing new antibacterial agents.

We investigated in this study the structure-activity relationship of S-benzylisothiourea derivatives and related compounds to define the structural element(s) required for inducing spherical cells in *E. coli*.

Materials and Methods

Anucleate cell blue assay. The anucleate cell blue assay was carried out as reported previously. Briefly, *E. coli* K-12 strain SH3210 (ΔtrpE5 his λ pXX747) was grown in a P medium containing 1% Polypepton and 0.5% NaCl (pH 7). Paper disks (φ 8 mm) each soaked with 20 μl of a sample solution were placed on P medium agar plates (1.5% agar) containing $10^4$ cells/ml of SH3210 and 40 μg/ml of 5-bromo-4-chloro-3-indolyl β-D-galactoside. The plates were incubated at 42° C. for 24 h, and the development of a blue color and the growth inhibitory zone around the paper disks were evaluated. The development of a blue color in this assay suggests the production of anucleate cells.

Microscopic observation. *E. coli* K-12 strain MG1655 (F$^-$ λ$^-$) was grown in Lennox broth containing 1% Polypepton, 0.5% yeast extract, 0.5% NaCl, and 0.1% glucose (pH 7.2). Cells spread on a slide glass were treated with methanol for 5 min and covered with poly-L-lysine. The fixed cells were observed by the differential interference contrast system through an Axioskop 2 microscope (Carl Zeiss Co., Ltd., Oberkochen, Germany). To observe the anucleate cells, cells were stained with a 4',6-diamidino-2-phenylindole (DAPI)

solution (5 µg/ml in saline) and then observed by the fluorescence phase-contrast combined method.

Chemical compounds. S-(3,4-Dichlorobenzyl)isothiourea, S-(4-chlorobenzyl)isothiourea, S-cyclohexylmethylisothiourea and S-heptylisothiourea were synthesized as described later. S-Benzylisothiourea, benzylthiocyanate and benzylisocyanate were purchased from Wako Pure Chemical Industries Ltd. (Osaka, Japan), benzylisothiocyanate from Avocado Research Chemicals Ltd. (Lancs, UK), thiourea, N-phenylthiourea and S-ethylisothiourea from Sigma-Aldrich Co. (St. Louis, Mo., USA). 3,4-Dichlorobenzyl chloride, 4-chlorobenzyl chloride, bromomethylcyclohexane and 1-chloroheptane were purchased from Tokyo Kasei Kogyo Co., Ltd. (Tokyo, Japan).

Synthesis of the compounds. Thiourea was suspended in dehydrated ethanol, and 3,4-dichlorobenzyl chloride was added to the suspension. The mixture was heated at 130° C. to reflux for several hours and then cooled to room temperature. The reaction mixture was concentrated under vacuum, and the resulting residue was diluted with methanol. The product was purified by recrystallization from diethyl ether. The structure of the compound was confirmed by $^1$H-NMR spectrometry. S-(4-Chlorobenzyl)isothiourea, S-cyclohexylmethylisothiourea and S-heptylisothiourea were similarly synthesized by using 4-chlorobenzyl chloride, bromomethylcyclohexane and 1-chloroheptane, respectively, instead of 3,4-dichlorobenzyl chloride.

Other bacterial strains used. *Bacillus subtilis* 168 was from laboratory stock. *Pseudomonas putida* NBRC14164 (the same as ATCC12633), *Salmonella typhimurium* NBRC13245 (the same as LT2), and *S. aureus* subsp. *aureus* NBRC15035 (the same as ATCC29213) were obtained from the National Institute of Technology and Evaluation (Kisarazu, Chiba, Japan).

Determination of minimum inhibitory concentration (MIC). MICs were also determined on Mueller Hinton agar plates (0.2% beef extract, 1.75% acid digest of casein, 0.15% soluble starch, 1.5% agar, pH 7.3). The same values were obtained for L agar plates and Mueller Hinton agar plates.

Results

In order to define the structural element(s) required for the activity to induce spherical cells in *E. coli*, the biological activity of two S-benzylisothiourea derivatives and seven related compounds, together with A22 (1), was examined in this study (Table 1).

TABLE 1

Summary of the Studies on the Structure-Activity Relationship of S-Benzylisothiurea Derivatives

| Compounds[a] | Anucleate cell blue assay (φ min)[b] | | MIC (µg/ml)[c] | | | | | Shape[d] |
|---|---|---|---|---|---|---|---|---|
| | Growth inhibition | Development of blue color | E. coli | P. putida | S. typhimurium | B. subtilis | S. aureus | |
| 1 (3,4-dichlorobenzyl structure) | 18 | 30 | 3.13 | 100 | 3.13 | 100 | >100 | Sphere* |
| 2 (4-chlorobenzyl structure) | 17 | 30 | 3.13 | >100 | 3.13 | >100 | >100 | Sphere* |
| 3 (benzyl structure) | 9 | 18 | 100 | >100 | >100 | >100 | >100 | Sphere* |
| 4 (cyclohexylmethyl structure) | — | — | >100 | >100 | >100 | >100 | >100 | Rod** |
| 5 (heptyl structure) | 12 | 18 | >100 | >100 | >100 | >100 | >100 | Rod** |

TABLE 1-continued

Summary of the Studies on the Structure-Activity Relationship of S-Benzylisothiourea Derivatives

| Compounds[a] | Anucleate cell blue assay (φ min)[b] | | MIC (μg/ml)[c] | | | | | Shape[d] |
|---|---|---|---|---|---|---|---|---|
| | Growth inhibition | Development of blue color | E. coli | P. putida | S. typhimurium | B. subtilis | S. aureus | |
| 6 (ethyl-S-C(NH)NH₂) | — | — | >100 | >100 | >100 | >100 | >100 | Rod** |
| 7 (benzyl-S-C≡N) | — | — | >100 | >100 | >100 | >100 | >100 | Rod* |
| 8 (benzyl-N=C=S) | 18 | — | 50 | >100 | 100 | 25 | 12.5 | Rod** |
| 9 (benzyl-N=C=O) | — | — | >100 | >100 | >100 | >100 | >100 | Rod** |
| 10 (phenyl-NH-C(S)-NH₂) | — | — | >100 | >100 | >100 | >100 | >100 | Rod** |

[a]1, A22, S-(3,4-dichlorobenzyl)isothiourea; 2, S-(4-chlorobenzyl)isothiourea; 3, S-benzylisothiourea; 4, S-cyclohexylisothiourea; 5, S-heptylisothiourea; 6, S-ethylisothiourea; 7, S-benzylithiocyanate; 8, benzylisothiocyanate; 9, benzylisocyanate; 10, N-phenylthiourea.
[b]The anucleate cell blue assay was carried out as described in Materials and Methods section. Values represent the diameters of growth inhibitory zones or blue color zones.
[c]MICs were determined for E. coli MG1655, P. putida NBRC14164 (the same as ATCC12633), S. typhimurium NBRC13245 (the same as LT2), B. subtilis 168, and S. aureus subsp. aureusNBRC15035 (the same as ATCC29213).
[d]Cell shape was examined for the E. coli MG1655 cultures treated with each compound at 3 □ MIC (*) or at 300 μg/ml (**) at 30° C. for 16 h.

Since 1 had originally been found through screening by an anucleate cell blue assay, the effect of each compound was first examined by this assay. The development of a blue color in the anucleate cell blue assay suggests the production of anucleate cells, and the formation of a growth inhibitory zone represents antibacterial activity.

S-(4-Chlorobenzyl)isothiourea (2) induced a deep blue zone around a growth inhibitory zone almost comparable to those of 1. S-benzylisothiourea (3) also developed a blue zone just around the paper disk, but only a marginal growth inhibitory zone was detected. These indicate that 3- and/or 4-chloro-substitution of the S-benzyl group was not absolutely required for the activity to induce a blue zone in this assay, but did enhance the activity. S-Cyclohexylmethyl-isothiourea (4) induced neither a growth inhibitory zone nor blue zone in this assay. Interestingly, S-heptylisothiourea (5) induced a growth inhibitory zone as well as a blue zone, but, as mentioned later, did not induce spherical cells. S-Ethyl-isothiourea (6) induced neither a growth inhibitory zone nor blue zone in this assay. These results indicate that the S-benzyl group was necessary to show activity for inducing blue zones in this assay (Table 1).

Benzylthiocyanate (7) and benzylisocyanate (9) induced neither a growth inhibitory zone nor blue zone. Benzylisothiocyanate (8) induced a growth inhibitory zone, but no blue zone developed around the growth inhibitory zone in this assay. N-Phenylthiourea (10) induced neither a growth inhibition nor blue zone. These results suggest that the isothiourea group was also necessary for the activity to induce blue zones. Judging from all these results, the S-benzylisothiourea structure was necessary and sufficient for the activity to develop a blue color in this assay (Table 1).

The MIC of each compound for E. coli and other several bacteria was determined. 1 showed antibacterial activity toward E. coli and S. typhimurium at a relatively low concentration (3.13 μg/ml), but was less effective against P. putida (100 μg/ml) and Gram-positive bacteria (100 μg/ml for B. subtilis and more than 100 μg/ml for S. aureus). 2 showed similar antibacterial activity to that of 1 against these bacteria (see Table 1). MIC of 3 was 100 μg/ml for E. coli and more than 100 μg/ml for the other bacteria tested. These results concur with those of the anucleate cell blue assay. Although 5 induced a growth inhibitory zone in the anucleate cell blue assay, MIC of 5 was more than 100 μg/ml for E. coli and for the other bacteria. The reason for this discrepancy is unclear, but it might have been due to the physical properties of 5 such as the diffusion efficiency of the compound in agar plates. 8 showed relatively strong antibacterial activity, this activity being stronger against Gram-positive bacteria than E. coli.

This suggests that the mode of action of 8 differed from that of the S-benzylisothiourea derivatives. MICs of compounds 4, 6, 7, 9 and 10 were each more than 100 μg/ml against all the bacteria tested (Table 1).

The effect of each compound on *E. coli* cell morphology was next examined. Exponentially growing *E. coli* MG1655 cultures were each treated with a compound at 3×MIC (for those that showed antibacterial activity) or at 300 μg/ml (for those that did not show antibacterial activity) at 30° C. for 16 hrs. Only the compounds having an S-benzylisothiourea structure, 2 and 3 in addition to 1, induced a spherical cell shape in *E. coli* (FIGS. 1*b-d*). *E. coli* cells treated with 4 seemed to be shorter than corresponding untreated cells, but spherical cells were not induced (FIG. 1*e*). 5 induced somewhat elongated cells, but not spherical cells (FIG. 1*f*). This means that the action mechanism of 5 to induce a blue zone in the anucleate cell blue assay was different from that of the S-benzylisothiourea derivatives. All other compounds showed little effect on *E. coli* cell morphology (FIGS. 1*g-k*). Spherical anucleate cells were only observed with those compounds having the S-benzylisothiourea structure. This again concurs well with the results of the anucleate cell blue assay.

We isolated the novel S-benzylisothiourea compound, A22, through screening by the anucleate cell blue assay. A22 induced spherical cells and spherical anucleate cells in *E. coli*. To define the essential structural element(s) required for inducing these phenomena in *E. coli*, the biological activities of two S-benzylisothiourea derivatives and seven related compounds, together with A22, were investigated in this study. It was only those compounds having the S-benzylisothiourea structure that showed activity to induce spherical cells in *E. coli*.

A22 was effective against Gram-negative rod-shaped bacteria. In fact, A22 induced spherical cells in *P. putida* and *S. typhimurium* as well as in *E. coli*, but did not in *B. subtilis*. 2 also showed similar effects, suggesting that this was a common feature of this series of compounds, probably due to permeability or target specificity.

The activity to induce spherical cells concurred well with that to induce a blue color in the anucleate cell blue assay, suggesting that spherical cell formation was accompanied by anucleate cell production. Anucleate cell production has also been observed in the case of the amidinopenicillin, mecillinam.[2] Mecillinam induced spherical cells in *E. coli* by inhibiting PBP 2. The spherical cells induced by these compounds varied in size. Asymmetric cell division has frequently been observed in cultures treated with A22 or mecilinam, suggesting that the loss of a rod shape leads to asymmetric cell division which results in anucleate cell production.

Genetic analyses have so far identified five genes, pbpA (a structural gene of PBP 2), rodA, mreB, mreC and mreD, that are involved in the process of rod shape formation in *E. coli*. Preliminary biochemical and physiological analyses have suggested that the target molecule of A22 was not PBP. A22 may therefore act on a rod-shape-determining protein(s) other than PBP2. It has recently been reported that the MreB protein had an actin-like structure and functioned as a cytoskeletal protein in the rod shape-determination mechanism. The functions of rodA, mreC and mreD are unknown as yet. A22 and other derivatives inducing spherical cells will be useful tools for analyzing the rod shape-determination mechanism in *E. coli*.

Studies on the structure-activity relationship revealed the essential active structure for inducing spherical cells and spherical anucleate cells in *E. coli* to be S-benzylisothiourea. It also seems that 3- and/or 4-chloro-substitution on S-benzyl group in S-benzylisothiourea enhanced the activity. It will be interesting to examine the effects of other modifications to the S-benzyl group. Since no antibacterial agent, except mecillinam, that acts on the rod shape-determination mechanism is known, S-benzylisothiourea is an attractive lead compound for developing new antibacterial agents having a new molecular target.

Example 2

The MIC of each compound listed below was tested for *E. coli*, *Pseudomonas putida*, *Salmonella typhimurium*, *Bacillus subtilis*, and *Staphylococcus aureus*, using the methods as described in Example 1.

| Compounds | | | E. coli | P. putida | S. typhimurium | B. subtilis | S. aureus | Shape |
|---|---|---|---|---|---|---|---|---|
| 4-Cl | (structure) | HCl | 3.13 | >100 | 3.13 | >100 | >100 | Sphere |
| 3-Cl | (structure) | HCl | 50 | >100 | >100 | 50 | >100 | Sphere |

-continued

| Compounds | | | MIC (μg/ml) | | | | | Shape |
|---|---|---|---|---|---|---|---|---|
| | | | E. coli | P. putida | S. typhi-murium | B. subtilis | S. aureus | |
| 2-Cl | [structure] | HCl | 12.5 | >100 | 25 | >100 | >100 | Sphere |
| 4-F | [structure] | HCl | 12.5 | >100 | 12.5 | 50 | 100 | Sphere |
| 3-F | [structure] | HCl | 50 | >100 | >100 | 50 | >100 | Sphere |
| 2-F | [structure] | HCl | 25 | >100 | 25 | >100 | >100 | Sphere |
| 4-CF$_3$ | [structure] | HCl | 50 | >100 | >100 | >100 | >100 | Sphere |
| 3-CF$_3$ | [structure] | HCl | >100 | >100 | >100 | >100 | >100 | Sphere |
| 2-CF$_3$ | [structure] | HCl | >100 | >100 | >100 | >100 | >100 | Sphere |
| 4-CH$_3$ | [structure] | HCl | 25 | >100 | 50 | >100 | >100 | Sphere |

-continued

| Compounds | | | MIC (µg/ml) | | | | | Shape |
|---|---|---|---|---|---|---|---|---|
| | | | E. coli | P. putida | S. typhimurium | B. subtilis | S. aureus | |
| 4-Br | | HBr | 3.13 | >100 | 6.25 | >100 | >100 | Sphere |
| 4-I | | HCl | 12.5 | >100 | 25 | >100 | >100 | Sphere |
| 4-NO₂ | | HCl | 25 | >100 | 50 | 25 | >100 | Sphere |
| 2,3-Cl | | HCl | 25 | >100 | 25 | 100 | 25 | Sphere |
| 2,4-Cl | | HCl | 1.56 | >100 | 1.56 | >100 | >100 | Sphere |
| 2,5-Cl | | HBr | 12.5 | >100 | 25 | >100 | >100 | Sphere |
| 2,6-Cl | | HCl | 12.5 | >100 | 25 | >100 | >100 | Sphere |
| 3,4-Cl | | HCl | 3.13 | 100 | 3.13 | 100 | >100 | Sphere |

-continued

| Compounds | | | MIC (µg/ml) | | | | | Shape |
|---|---|---|---|---|---|---|---|---|
| | | | E. coli | P. putida | S. typhi-murium | B. subtilis | S. aureus | |
| 3,5-Cl | | HCl | >100 | >100 | >100 | >100 | >100 | Sphere |
| 2,4,6-Cl | | HCl | 100 | >100 | >100 | 100 | >100 | Sphere |
| 2,6-F | | HCl | 50 | >100 | 50 | >100 | >100 | Sphere |
| 3,4-F | | HCl | 12.5 | >100 | 25 | 25 | 100 | Sphere |
| pentaF | | HCl | >100 | >100 | >100 | >100 | >100 | Sphere |
| 2,4-Cl 5-F | | HCl | 0.78 | >100 | 12.5 | 12.5 | >100 | Sphere |
| Benzyl | | HCl | 100 | >100 | >100 | >100 | >100 | Sphere |
| cHex | | HBr | >200 | >200 | >200 | >200 | >200 | Short Rod |
| Hep | | HCl | 200 | 200 | >200 | >200 | >200 | Rod |

-continued

| Compounds | | | MIC (μg/ml) | | | | | | Shape |
|---|---|---|---|---|---|---|---|---|---|
| | | | | E. coli | P. putida | S. typhi-murium | B. subtilis | S. aureus | |
| Ethyl | (structure) | | HBr | >100 | >100 | >100 | >100 | >100 | Rod |
| DMU | (structure) | | | >100 | >100 | >100 | >100 | >100 | Rod |
| IM | (structure) | | | >100 | >100 | >100 | >100 | >100 | Rod |
| TZ | (structure) | | | >100 | >100 | >100 | >100 | >100 | Rod |
| 2-Br | (structure) | | HBr | 50 | >100 | 50 | >100 | >100 | Sphere |
| 4-MeO | (structure) | | HCl | >100 | >100 | >100 | >100 | >100 | Sphere |
| 4-Cl Pyr | (structure) | | HCl | 100 | >100 | >100 | >100 | >100 | Sphere |
| BTC | (structure) | | | >100 | >100 | >100 | >100 | >100 | Rod |
| BITC | (structure) | | | 50 | >100 | 100 | 25 | 12.5 | Rod |

-continued

| Compounds | | MIC (µg/ml) | | | | | Shape |
|---|---|---|---|---|---|---|---|
| | | E. coli | P. putida | S. typhi-murium | B. subtilis | S. aureus | |
| BIC | (structure) | >100 | >100 | >100 | >100 | >100 | Rod |
| PTU | (structure) | >100 | >100 | >100 | >100 | >100 | Rod |
| MPC | (structure) | 0.0977 | >100 | 0.0977 | 12.5 | 50 | Sphere |
| TC | (structure) | 3.13 | 6.25 | 3.13 | 6.25 | 0.781 | Rod |
| ABPC | (structure) | 3.13 | >100 | 1.56 | 0.0488 | 0.195 | Fil |
| PCG | (structure) | 50 | >100 | 12.5 | 0.0122 | 0.0977 | Fil |
| CP | (structure) | 6.25 | 50 | 6.25 | 3.13 | 12.5 | Rod |
| SPFX | (structure) | 0.0244 | 0.391 | 0.0488 | 0.0244 | 0.0488 | |

Example 3

Faithful chromosome segregation is an essential component of cell division in all organisms. The eukaryotic mitotic machinery uses the cytoskeleton to move specific chromosomal regions. To investigate the potential role of the actin-like MreB protein in bacterial chromosome segregation, we first demonstrate that MreB is the direct target of the small molecule A22. We then demonstrate that A22 completely blocks the movement of newly replicated loci near the origin of replication but has no qualitative or quantitative effect on the segregation of other loci if added after origin segregation. MreB selectively interacts, directly or indirectly, with origin-proximal regions of the chromo-some, arguing that the origin-proximal region segregates via an MreB-dependent mechanism not used by the rest of the chromosome.

Demonstrating a direct role for MreB in chromosome segregation has proven difficult. MreB loss of function is lethal and pleiotropic, disrupting multiple cellular processes distinct from chromosome dynamics, including cell shape determination, polar protein localization, and cell division. Thus, it remains unclear whether MreB plays a primary role in chromosome segregation, or if MreB's effect on chromosome dynamics is a secondary consequence of other functions.

Here we present the first evidence that supports a direct role for MreB in the segregation of a specific region of the chromosome. We reached these conclusions by first characterizing a small molecule, A22, that specifically, rapidly, and reversibly perturbs MreB function. Our studies focus on the differentiating bacterium, *Caulobacter crescentus*, whose ability to be synchronized renders it particularly powerful for the analysis of chromosome segregation. By administering the MreB-perturbing compound at different stages of the *Caulobacter* cell cycle we show that origin-proximal loci segregate through an MreB-dependent mechanism, and that the rest of the chromosome follows the origin using an MreB-independent mechanism. The ability of A22 to block DNA segregation without affecting DNA replication also demonstrates that the process of replication is not sufficient to separate chromosomes, as was previously proposed. Finally, we used chromatin immunoprecipitation assays to demonstrate a specific physical association between MreB and origin-proximal loci. Together, these results suggest that *Caulobacter* chromosome segregation is mediated by a cytoskeletally driven mechanism, with regions near the origin functioning as a centromere.

Figure 2:
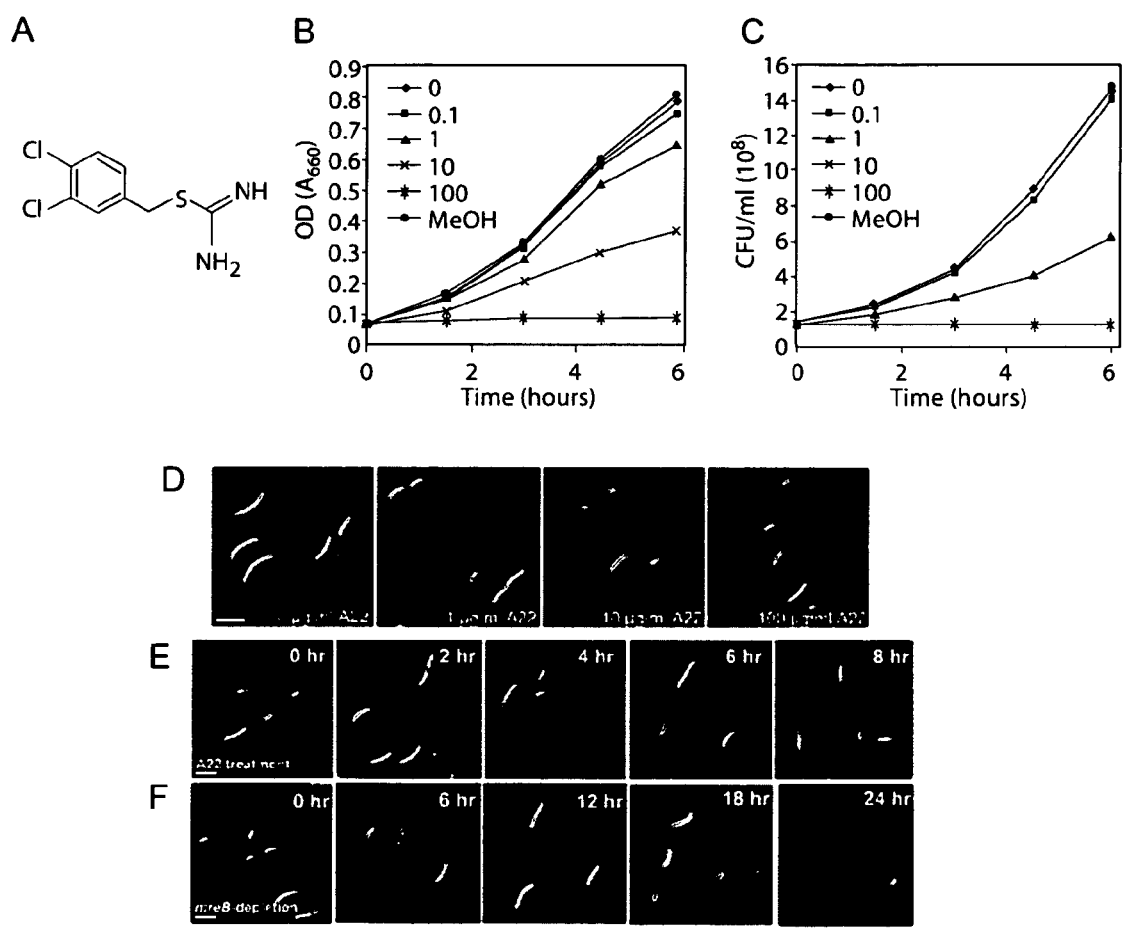
FIG. 2A-2F. A22 Affects *Caulobacter* Growth and Morphology. (A) The chemical structure of S-(3,4-dichlorobenzyl)isothiourea, A22. (B) Growth curve of cells treated for up to 6 hr with 0, 0.1, 1, 10, and 100 µg/ml of A22 or an equivalent volume of methanol (MeOH). (C) Colony formation assay curve for cells treated with 0, 0.1, 1, 10, and 100 µg/ml of A22 or an equivalent volume of methanol (MeOH). (D) DIC images of *Caulobacter* grown for 6 hr in 0, 1, 10, or 100 µg/ml of A22. (E) Timecourse of cells grown in 10 µg/ml of A22 for 0, 2, 4, 6, and 8 hr. (F) Timecourse of cells depleted of mreB for 0, 6, 12, 18, and 24 hr. Scalebars represent 1 µm.

Results dichlorobenzyl)isothiourea; FIG. 2A) was identified through a screen for chemicals that induce the formation of anucleate *E. coli* cells.

Addition of A22 to *Caulobacter* cultures slowed growth in a dose-dependent fashion (FIG. 2B). Similar volumes of solvent (methanol) alone had no effect on growth. In cultures with a normal generation time of 87 min in rich PYE medium, a decline in growth rate was observed as early as 30 min after A22 treatment, suggesting that A22 rapidly exerts its effects on the cell. This rapid effect on cell growth could be due to a disruption in cell wall deposition or could reflect a secondary response to some other cellular perturbation.

To assess the impact of A22 on cell division and survival, we examined the effect of A22 on colony formation. At 10 μg/ml and higher, A22 completely halted the increase in CFU, without causing it to diminish (FIG. 2C), consistent with a block in cell division that is bacteriostatic but not bactericidal. At a concentration of 1 μg/ml, A22 partially slowed colony formation, and at 0.1 μg/ml or methanol alone, colony formation was un-perturbed (FIG. 2C).

Consistent with previous observations in *E. coli* (Iwai et al., 2002), A22 caused a dose-dependent alteration of *Caulobacter* morphology, transforming normal, crescent-shaped cells into rounded, lemon-shaped cells. The progression of cell shape deformation by A22 treatment was qualitatively similar to that caused by mreB depletion, though the A22 effect was more rapid (FIGS. 2D-1F). At 0.1, 1, and 10 μg/ml, A22 both slowed cell growth and altered cell shape, while treatment with 100 μg/ml A22 completely blocked growth but did not cause *Caulobacter* to round up (FIG. 2D). This result suggests that the manifestation of A22's effect on morphol-

TABLE 1 mreB Mutations Confer A22 Resistance

| Mutation | Times Isolated | Doubling Time in A22* | Doubling Time without A22* | Doubling in A22 when Replaced by WT mreB* | Doubling in A22 in WT Genetic Background* |
|---|---|---|---|---|---|
| None (wt) | — | 148' | 87' | 145' | 156' |
| T167A | 10 | 110' | 114' | 148' | 105' |
| V324A | 5 | 113' | 112' | 142' | 115' |
| D192G | 1 | 118' | 120' | 145' | 116' |
| A325P | 1 | 116' | 120' | 144' | 115' |
| D16G | 1 | 115' | 118' | 150' | 112' |
| P112S | 1 | 118' | 117' | 146' | 119' |
| L23R | 1 | 121' | 124' | 145' | 120' |

*All doubling times refer to increased cell mass over a period of 6 hr as measured by optical density (A660). Wild-type (wt) cells do not divide in the presence of A22.

A22 Is a Small Molecule that Affects *Caulobacter* Growth and Morphology. To dissect the cellular activities of *Caulobacter* MreB, we sought a method to acutely perturb MreB function. mreB mutants are lethal, and genetically depleting mreB is slow, requiring multiple cell cycles before MreB protein levels are significantly reduced. For a faster method of disrupting MreB function we explored the use of small molecules, an approach that has proven highly successful for dissecting the functions of the eukaryotic cytoskeleton. Treatment of *Caulobacter* with drugs, including cytochalasin D, latrunculin, jasplakinolide, and phalloidin, that affect eukaryotic actin failed to perturb growth rate or morphology, suggesting that they either do not affect MreB or cannot enter *Caulobacter* cells. One small molecule that was known to affect bacteria, A22, showed more promise. A22 (S-(3,4- ogy requires cell growth. For example, A22 could disrupt the localization of new cell wall synthesis but have no effect on the existing cell wall, such that without additional growth and wall synthesis A22's effects cannot be perceived. A dependence on cell growth could also explain why A22's effect on morphology takes several hours to manifest.

MreB Is the Direct Target of A22. To identify the cellular target(s) of A22, we carried out a screen for A22-resistant mutants by growing large numbers of *Caulobacter* on plates containing 10 μg/ml A22. We independently isolated 20 mutants that stably and repeatedly formed colonies on plates containing 10 μg/ml A22 and grew in liquid culture containing 10 μg/ml A22. Since MreB was proposed as a possible target of A22, we PCR-amplified and sequenced the mreB gene in the 20 A22-resistant strains and a control wild-type strain. Each of the 20 A22-resistant strains contained a single missense point mutation in its mreB gene, whereas the wild-type A22-sensitive strain had no mreB point mutations (Table 2). Though isolated independently, the 20 strains had only 7 different point mutations: one specific point mutation was found in 10 of the strains, another specific point mutation was found in 5 of the strains, and 5 additional point mutations were found in 1 strain each. Since all 7 of these mutations affected amino acids that are conserved between *Caulobacter* MreB and *Thermotoga maritima* MreB, they could be mapped onto the solved three-dimensional structure of *T. maritima* MreB. Interestingly, 5 of the 7 mutated residues are located in MreB's ATP binding site, and the remaining 2 residues reside side-by-side in a helix that also contacts the nucleotide, suggesting that A22 may interact with MreB's nucleotide binding pocket (FIGS. 3A and 3B). All of the resistant strains grow at a similar rate in rich PYE medium (w115 min/doubling), which is slower than wild-type cells without drug (87 min/doubling), but they are largely unaffected by the presence of A22 (w115 min/doubling) (Table 2). All of the resistant strains also exhibit a slightly abnormal morphology, with cells that were uncharacteristically straight and long, and exhibited occasional kinks (FIG. 3C). The perturbation in cell shape is consistent with an effect on MreB's role in cell-shape determination, and the phenotypic similarity of all 20 strains suggests a common mode of action, such as altering the MreB nucleotide binding pocket.

To determine if each of these mutations in mreB was necessary for A22 resistance, an apramycin-resistance cassette was integrated immediately upstream of the mreB gene in wild-type cells. Phage transduction and apramycin selection thus enabled the replacement of the A22-resistant mreB mutant loci with wild-type mreB. In all 20 cases, this manipulation caused the A22-resistant strains to become A22 sensitive, suggesting that a mutation linked to mreB is necessary for A22 resistance (Table 2). Conversely, the same apramycin-resistance cassette was also integrated upstream of each of the seven different A22-resistant mreB loci. Phage transduction was used again, this time to replace the mreB loci of wild-type strains with the mutant mreB. In each case, the resulting strains became A22 resistant, indicating that each of these mreB mutations is sufficient to confer resistance, and suggesting that there are no unlinked mutations in the strain backgrounds that are necessary for resistance (Table 21). Thus, mreB missense alleles appear to be necessary and sufficient for A22 resistance.

A22 Rapidly and Reversibly Delocalizes GFP-MreB. During the *Caulobacter* cell cycle, MreB forms a lengthwise spiral in swarmer cells and stalked cells. It then appears to condense into an increasingly tight ring positioned at the future site of cell division. When cytokinesis initiates, this ring is replaced by a lengthwise spiral, such that upon cell division each daughter cell inherits a fully expanded spiral. GFP-MreB expressing strains exhibit regularly spaced puncta and bands that resolve into three-dimensional spirals and rings when examined by deconvolution microscopy. Treatment with 10 or 100 μg/ml of A22 completely disrupted this GFP-MreB localization, resulting in cells with diffuse fluorescence that contain no discernable puncta or bands (FIG. 3A). MreB puncta and bands were largely maintained when cells were treated with 1 μg/ml or less of A22. Since 10 μg/ml of A22 strongly delocalizes GFP-MreB and blocks cell division without completely inhibiting cell growth, we have chosen to focus most of our subsequent A22 studies on this concentration.

Figure 3:
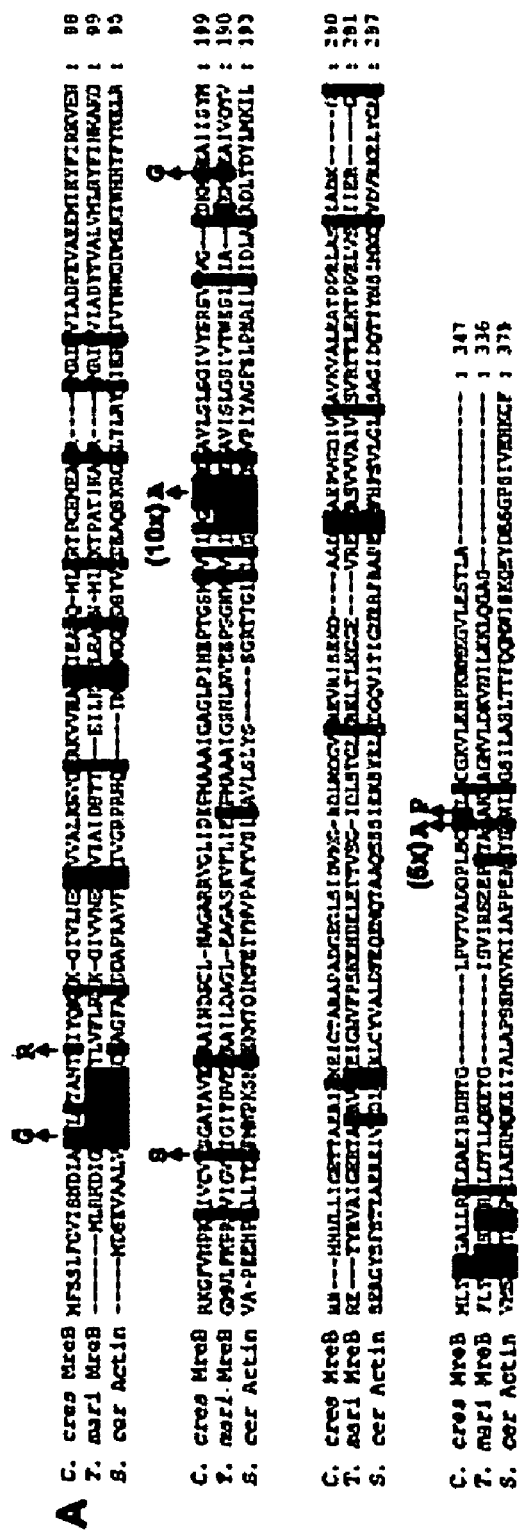
FIG. 3. A22-Resistant mreB Mutations Map to the Nucleotide Binding Pocket of MreB. (A) A Clustal W alignment of the *Caulobacter* (*C. cres*), *Thermotoga maritima* (*T. mari*), and *Saccharomyces cerevisiae* (*S. cer*) MreB/Actin proteins. Perfectly conserved residues are highlighted in gray and/or printed with white characters. The residues that form the active sites in the crystal structures of the *T. maritima* and *S. cerevisiae* proteins are highlighted in red. The residues that are mutated in the 20 A22-resistant *Caulobacter* strains are highlighted in green, and the corresponding mutation is denoted with an arrow. The mutations that were identified multiple times are identified with the number of occurrences in parentheses. (B) The *T. maritima* residues that correspond to those mutated in A22-resistant strains are highlighted in green in its crystal structure. The AMPPNP ligand in this MreB structure is highlighted in red. Shown are two rotational views of the same structure. (C) DIC (left) and fluorescence (right) images of cells expressing the T158A A22-resistant mreB allele fused to gfp. (D) Fluorescence image of T158A GFP-MreB-expressing cells that have been treated with 10 µg/ml A22 for 10 min. Scalebars represent 1 µm.
Figure 3:
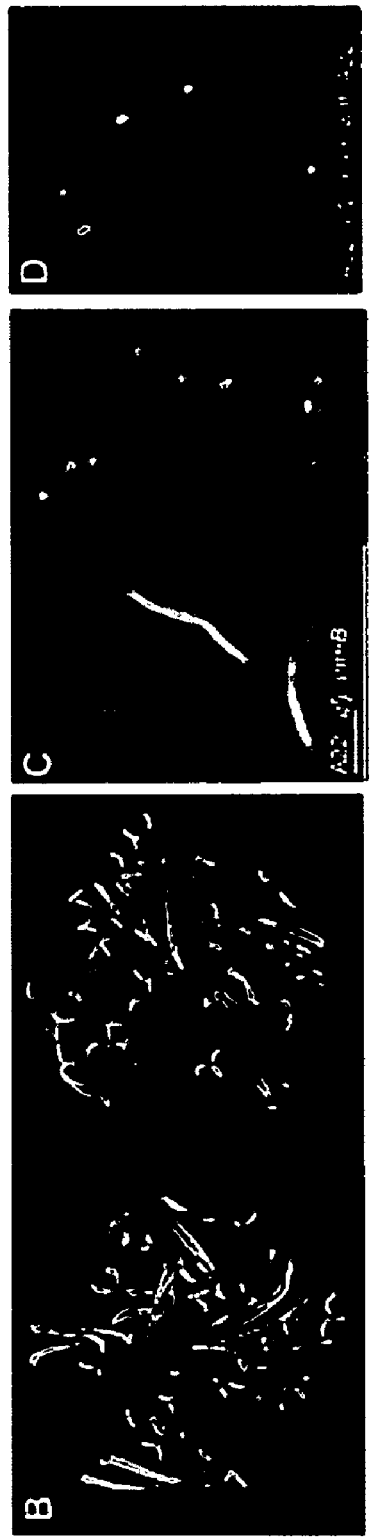
Figure 4:
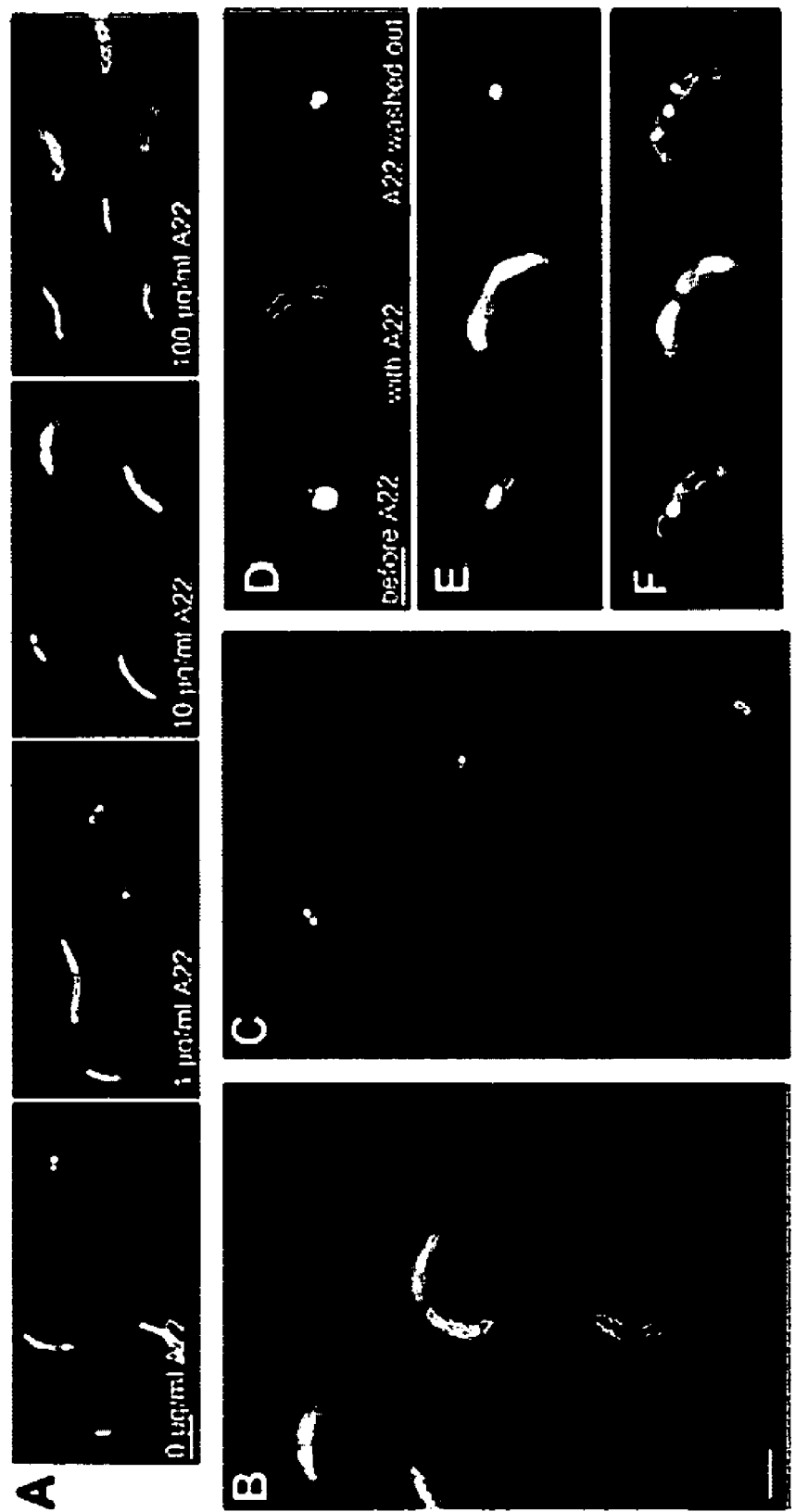
FIG. 4. A22 Rapidly and Reversibly Delocalizes GFP-MreB. (A) DIC (left) and fluorescence (right) images of GFP-MreB-expressing *Caulobacter* grown for 1 hr in 0, 1, 10, or 100 µg/ml of A22 imaged on agarose pads containing the same concentration of A22. (B) Fluorescence image of GFP-MreB-expressing *Caulobacter* imaged after being mounted on an agarose pad containing 10 µg/ml of A22 for 1 min, with no previous incubation with A22. (C) Fluorescence image of GFP-MreB-expressing *Caulobacter* that have been treated with 10 µg/ml A22 for 1 hr and then mounted for 1 min onto an agarose pad that does not contain A22. (D-F) Timelapse images of individual *Caulobacter* cells expressing GFP-MreB at three different cell cycle stages: an early predivisional cell with a tight medial MreB ring (D), a mid-predivisional cell with an expanding MreB ring (E), and a late predivisional cell with an expanded MreB spiral (F). These cells were imaged in a flow chamber to which they were attached with polylysine. For each series, the image on the left is taken before A22 treatment, the image in the middle is taken 1 min after washing in 10 µg/ml A22, and the image on the right is taken 2 min after washing in medium lacking A22. Scalebars represent 1 µm.

The onset of A22's effect on GFP-MreB is very rapid: within 1 min the GFP-MreB already delocalized (FIG. 4B). A22's effect on GFP-MreB is also rapidly reversible. Diluting the A22 concentration of cells treated with A22 for 1 hr by mounting them on pads lacking A22 leads to a full recovery of MreB localization within 1 min (FIG. 4C). GFP-MreB was monitored in the same cells before, during, and after A22 treatment by timelapse imaging cells in a flow chamber that allows A22 to be washed in and out (FIGS. 4D-4F). A22 delocalized both MreB spirals (puncta) and rings (bands), though MreB rings took longer to delocalize completely, suggesting that they may be more stable or may consist of more MreB filaments than the spirals. Cells generally retained a memory of the MreB structure present before A22 treatment (FIGS. 4D-3F). Cells with rings recovered rings, cells with spirals recovered spirals, and cells with partially compacted rings recovered partially compacted rings. These findings are consistent with MreB's localization being determined by extrinsic factors regulated by the cell cycle state, rather than an intrinsic MreB localization cycle.

We constructed a fusion of the most common A22-resistant mreB missense mutation (T158A) to GFP and asked if the cellular organization of this MreB mutant is maintained in 10 μg/ml of A22. This fusion was expressed in the corresponding A22-resistant strain, producing merodiploid cells containing both GFP-tagged and -untagged mutated mreB, but no wild-type mreB. These cells still exhibited a punctate MreB localization but did not appear to fully condense their spirals into rings (FIG. 3C). Since this mutation in the MreB ATP binding pocket perturbs MreB dynamic localization, nucleotide hydrolysis may play a role in regulating MreB dynamics. The localization of the mutated GFP-MreB was completely unaffected by treatment with A22 (FIG. 3D). Together, all of these results strongly suggest that MreB is the target of A22.

A22 Treatment Blocks Chromosome Segregation. Having established that A22 targets MreB and rapidly disrupts its localization, we used A22 to assess the acute role of MreB in chromosome segregation. To this end we took advantage of strains previously generated in our group that use the fluorescent repressor-operator system (FROS) to simultaneously label two specific chromosomal loci in the same living cell. This system uses fusions of two DNA binding proteins, the lac repressor (LacI) and the Tet repressor (tetR), to CFP and YFP, respectively. Two arrays, each containing multiple tandem repeats of either the LacI or TetR binding sites, are integrated into different chromosomal loci. Each fusion protein clusters at its respective array, causing the cellular address of that array to fluoresce in a detectable fashion.

Figure 5:
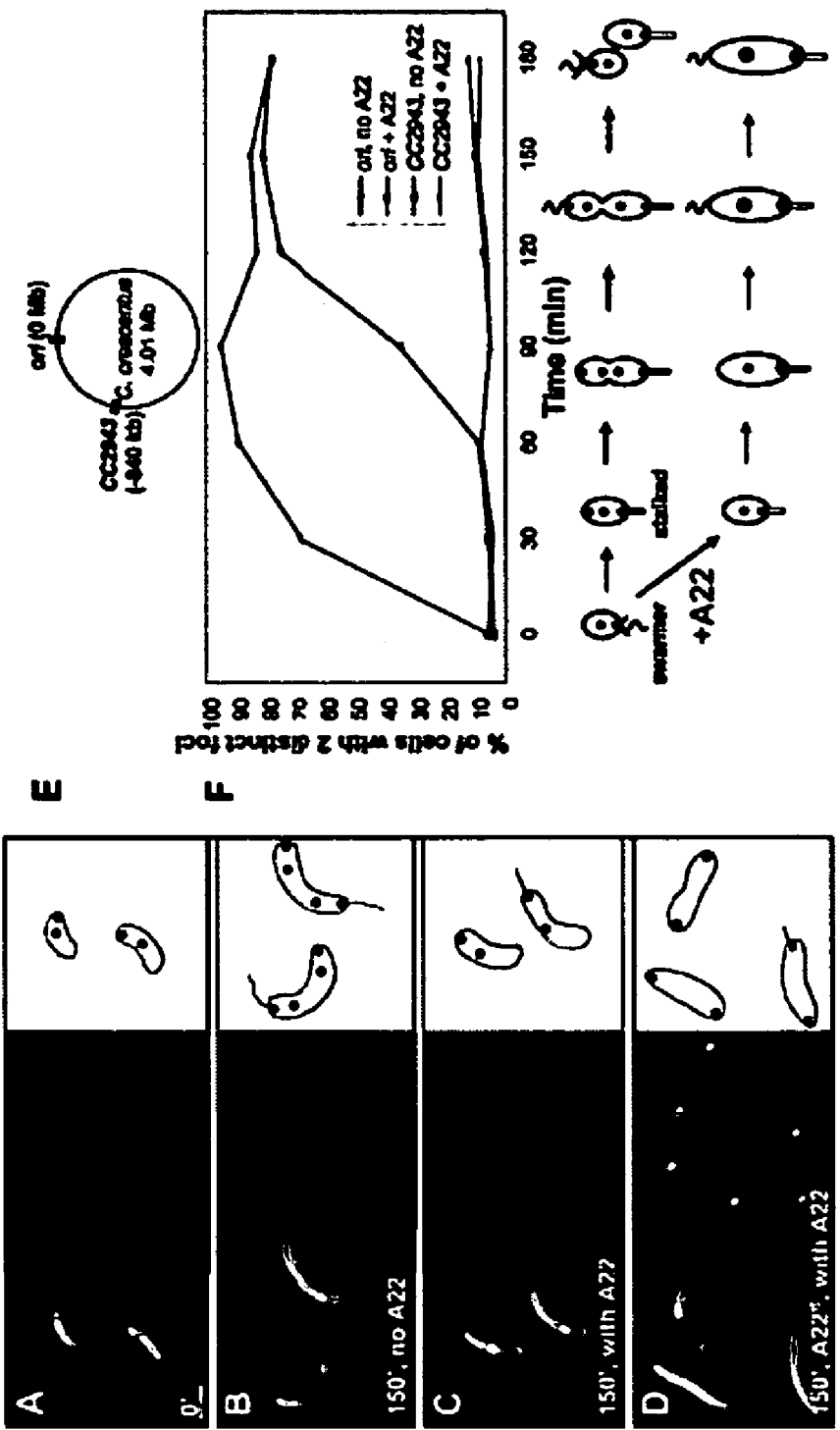
FIG. 5. Treatment of Swarmer Cells with A22 Blocks DNA Replication and/or Chromosome Segregation. To determine A22#s effect on chromosome segregation, swarmer cells doubly labeled at their origins (green) and the CC2943 locus (red) were isolated and incubated in the presence of A22. (A-C) DIC (left), YFP+CFP overlayed fluorescence (right), and schematic (right) images. LacI-CFP is bound to lacO arrays integrated at the origin and is shown in green in the overlay. TetR-YFP is bound to tetO arrays integrated at CC2943 and is shown in red in the overlay: (A) isolated swarmer cells, (B) cells grown synchronously for 150 min in medium lacking A22, and (C) containing 10 µg/ml A22. (D) Swarmer cells from T158A A22-resistant *Caulobacter* with labeled origins were isolated and incubated for 150 min in 10 µg/ml A22. Shown are DIC (left) and CFP fluorescence images of LacI-CFP bound to the origin. (E) Schematic of the genetic positions of the origin and CC2943 in the *Caulobacter* genome. (F) Percentage of doubly labeled origin and CC2943 FROS cells with two distinct foci at different times after synchrony and growth with or without A22. At least 75 cells were analyzed for each time point, with standard deviations of 3%-5%. Below the graph is a schematic illustration of what is observed without A22 (top line) and with A22 (bottom line). The green dots represent the origin and the red dots represent A22. Scalebars represent 1 µm.

At each division, *Caulobacter* divides asymmetrically to produce daughters with distinct morphologies and cell fates: a stalked cell that initiates DNA replication and a G1-arrested swarmer cell (see diagram in FIG. 5). The swarmer cell later differentiates into a stalked cell, at which time DNA replication initiates. Highly purified populations of swarmer cells can be isolated by density centrifugation and they then synchronously progress through the cell cycle once resuspended in fresh medium. Swarmer cells contain only one chromosome, oriented such that the origin of replication is at the flagellated pole, the terminus is at the other pole, and all other loci are linearly arrayed in between. Soon after replication initiation, one of the duplicated origins moves rapidly to the opposite pole while the other origin remains at its original pole. Other loci are then sequentially replicated and segregated to their correct final cellular positions.

Synchronized swarmer cells with lac arrays at the origin locus and tet arrays at the midcell-positioned CC2943 locus (FIG. 5A) were incubated with 10 μg/ml A22. After varying periods of time in the presence of A22, the cellular positions of the origin and CC2943 were examined by fluorescence microscopy. The cultures continued to increase in cell mass, as measured by an increase in optical density, but cell division was blocked. Although two duplicated and segregated loci were observed in untreated cells at time points from 30-180 min, the A22-treated cells continued to exhibit only one focus for each locus (FIGS. 5B, 5C, and 5F). This effect was reversible, since upon washing out the A22 drug, the origins were rapidly and normally segregated. The origin successfully segregated when this experiment was repeated with cells whose wild-type mreB locus was replaced with the T158A A22-resistant mreB allele (FIG. 5D). This result confirms that A22 affects chromosome segregation by acting on MreB and not another target.

A22 Does Not Block DNA Replication. Two scenarios could explain the A22-induced persistence of single origin and CC2943 foci. Either the chromosome never replicated such that the foci represent the original single copy of each locus, or the chromosome was replicated but failed to segregate such that both copies of each locus remain stuck together and cannot be resolved. We thus used several independent assays to distinguish between A22 impairment of DNA replication or chromosome segregation.

Figure 6:
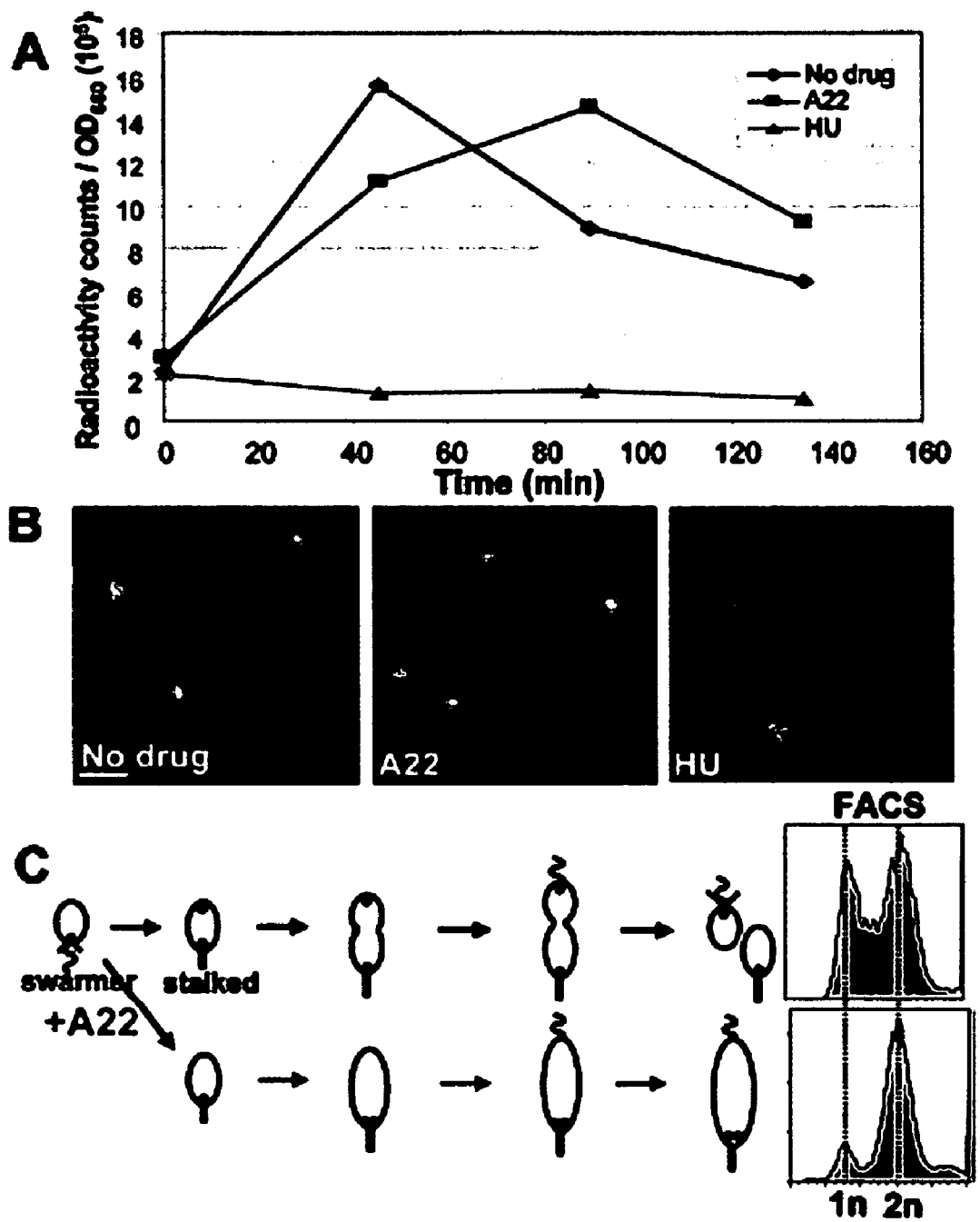
FIG. 6. A22 Does Not Block DNA Replication (A) DNA synthesis measured by the incorporation of 32P-radiolabeled dGTP relative to OD660 in synchronized cells grown for varying lengths of time in no drug, 10 µg/ml A22, or 5 mg/ml HU. (B) Fluorescence images of HoIB-GFP-expressing *Caulobacter* grown for 1 hr in no drug (left), 10 µg/ml A22 (middle), and 5 mg/ml HU (right). (C) A schematic illustrating the proposed effect of A22 treatment on origin (green) duplication and movement. To the right of each schematic is the FACS analysis of cells treated for 8 hr with or without 10 µg/ml A22. The dotted lines represent the one chromosome and two chromosome peaks. Scale bars represent 1 µm.

We first examined the incorporation of radiolabeled dGTP into DNA, which linearly correlates with the rate of DNA replication. Asynchronous cultures incorporated the same level of radioactivity regardless of whether or not they were treated with A22, directly demonstrating that A22 does not interfere with bulk DNA synthesis. To assess the effect of A22 on DNA replication during the cell cycle, the radiolabeled nucleotide incorporation assay was repeated using synchronized cultures at different points in the cell cycle. Untreated cells display a dramatic rise in radioactivity levels characteristic of DNA replication initiation at the swarmer-to-stalked cell transition. This rise in radioactivity levels was also observed in A22-treated cells (FIG. 6A). A22 treatment slightly delayed replication initiation, though this delay is insufficient to explain A22's dramatic inhibition of chromosome movement. Cells treated with hydroxyl-urea (HU), a replication inhibitor, exhibited no such increase in radioactivity levels (FIG. 6A).

To assess the ability of these cells to assemble a replisome at the replication origins, A22 was administered to cells expressing a fusion of GFP to the HolB subunit of DNA polymerase. Known inhibitors of DNA replication, HU (FIG. 6B) and novobiocin, can cause the rapid delocalization of HoIB-GFP. One hour of A22 treatment, however, had no effect on HoIB-GFP localization (FIG. 6B), demonstrating that A22 allows the replisome to form.

Finally, we examined the DNA content of A22-treated cells by FACS. Whereas untreated cultures contain cells with a distribution of DNA content from one to two chromosomes, A22-treated cultures predominantly contained cells with two chromosomes (FIG. 6C). Cells incubated with A22 failed to divide, as indicated in the diagram shown in FIG. 6C. A22-treated cells thus initiate and finish replication but do not divide or reinitiate replication, suggesting either the presence of a segregation defect-induced cell cycle checkpoint or an independent role of MreB in cell division.

Since A22 blocks neither the initiation nor the progression of DNA replication, we conclude that cells labeled at the origin and CC2943 and treated with A22 actually contained two copies of each of these loci. Since only one focus was observed for each, these foci must have contained two tightly associated, unsegregated loci. A22 thus appears to block chromosome segregation when added to cells prior to the replication and polar movement of the origin. Moreover, the act of DNA replication in and of itself seems to be insufficient to move two loci apart.

Figure 7:
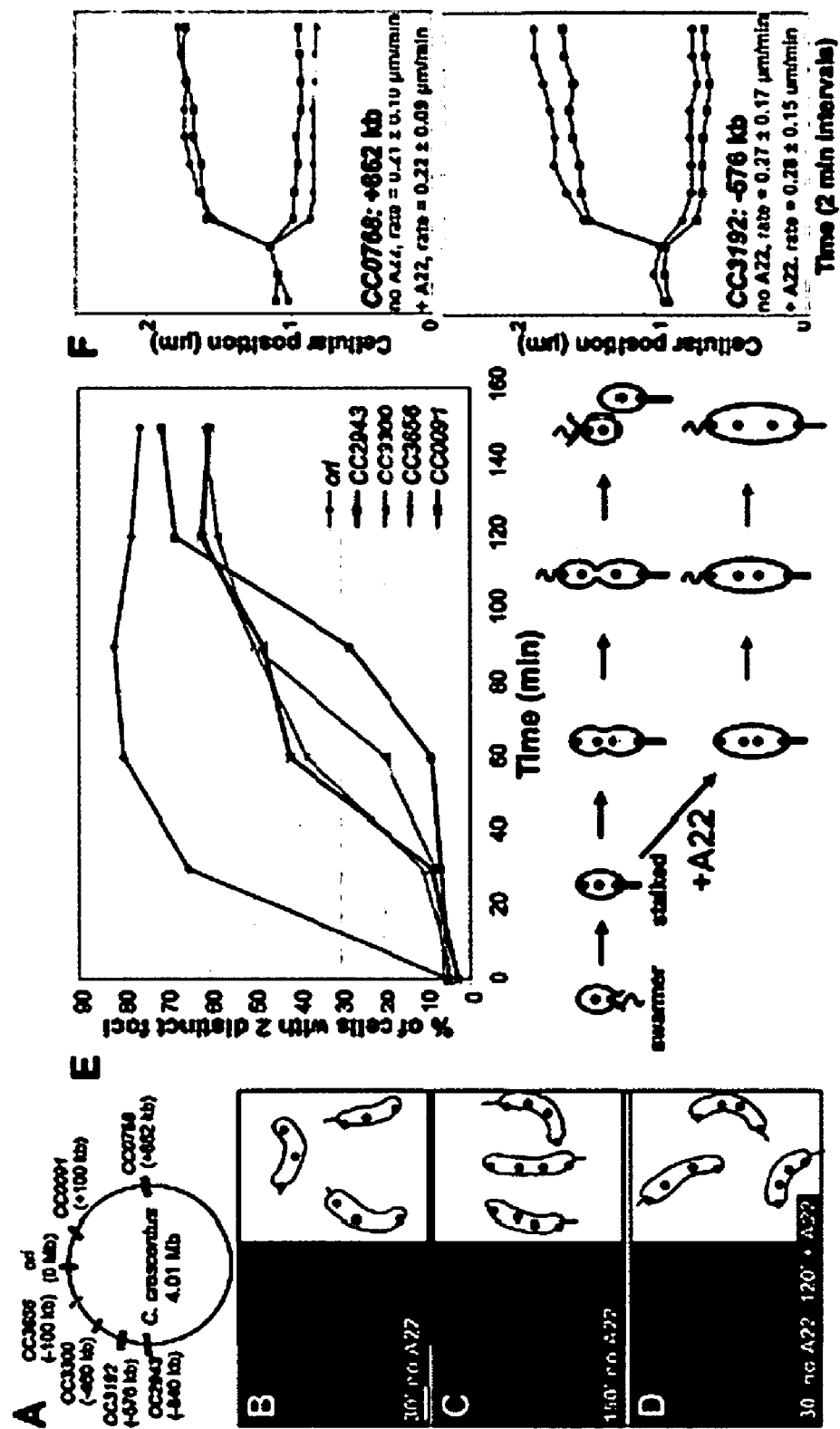
FIG. 7. A22 Does Not Block the Movement of Origin-Distal Loci (A) Schematic of the genetic positions of the origin and the other loci examined. (B-D) YFP+CFP overlayed fluorescence images (left) and schematic illustrations (right). LacI-CFP is bound to lacO arrays integrated at the origin and is shown in green in the overlay. TetR-YFP is bound to tetO arrays integrated at CC2943 and is shown in red in the overlay. Cells were synchronized and grown for 30 min without drug (B) and an additional 120 min with either no drug (C) or 10 µg/ml A22 (D). Scale bars represent 1 µm. (E) Percentage of cells that are doubly labeled at the origin and CC2943, CC3300, CC3656, or CC0091 with two distinct foci at different times after synchrony, growth for 30 min without drug, and subsequent growth in 10 mg/ml A22. At least 75 cells were analyzed for each time point, with standard deviations of 3%-5%. Below the graph is a schematic illustration of what is observed without A22 (top line) and with A22 (bottom line). The green dots represent the origin and the red dots represent A22. (F) Graphs depicting the average cellular position (distance from the stalked pole) at 2 min time intervals of loci labeled with lacO at CC0768, 862 kb to the right of the origin (top) and CC3192, 576 kb to the left of the origin. Loci from cells incubated without A22 are shown in brown, and loci from cells incubated with 10 µg/ml A22 are shown in blue. Position and rate analysis was performed as previously described.

A22 Treatment Does Not Perturb the Segregation of Origin-Distal Loci. Treatment of swarmer cells with A22 before the origins have segregated blocks the movement of chromosomal loci. But what happens when A22 is delivered after the origins have replicated and moved to opposite poles? To address this question, cells double-labeled at the origin and CC2943 were synchronized (FIGS. 7A and 7B). This time, however, we did not immediately treat the swarmer cells with A22 but rather waited until the duplicated origins had moved to the poles (30 min) before adding A22. At this point in the cell cycle, the CC2943 locus has yet to replicate. Consequently, such cells exhibit two origin foci but only one CC2943 focus. Surprisingly, these cells proceeded to replicate and separate their CC2943 locus into two foci (FIG. 7). The ability of the CC2943 locus to duplicate and separate in the presence of A22 supports the conclusion that A22 does not block replication. In addition, this result suggests that the origin and CC2943 move apart through separate sequential mechanisms, with the origin being A22 dependent and CC2943 A22 independent.

Since the origin and CC2943 differ in their dependence on A22 for segregation, similar experiments (in which A22 was added to synchronized cultures after the origin had duplicated and moved poleward) were performed on cells doubly labeled at their origins and sites in between CC2943 (840 kb to the left of the origin) and the origin. One of these strains was fluorescently tagged at CC3300 (460 kb to the left of the origin), and one at CC3656 (100 kb to the left of the origin) (FIG. 7A). These loci behaved just like CC2943: they duplicated and separated in the presence of A22 so long as the drug was administered after origin segregation (FIG. 7E). An additional locus 100 kb to the right of the origin (CC0091) was also not dependent on A22 for the separation of its loci following duplication (FIG. 7E). Thus, A22 appears to affect the separation and movement of only a relatively small portion of the genome located near the origin.

Though origin-distal loci can separate in the presence of A22, MreB could still partially contribute to their cellular positioning and rate of movement across the cell. Technical considerations prevent the quantitative analysis of locus movement in doubly labeled cells. Thus, to quantitatively assess the role of MreB in origin-distal locus segregation, we examined two singly labeled strains, one with CC0786 marked at 860 kb to the right of the origin, and one with CC3192 marked at 576 kb to the left of the origin. These cells were synchronized and grown in medium lacking A22 for 50 min, a length of time that has been previously established as more than sufficient to allow origin duplication and segregation. After 50 min, A22 was added, the cells were mounted onto agarose pads containing A22, and they were timelapse imaged for 60 min, with pictures taken every 2 min. The timelapses were analyzed using automated software that provides the absolute position of each locus in each cell. Time-lapse series for 15 cells were averaged (FIG. 7F) to obtain a rate of segregation. For both loci examined, both locus position and rate of segregation were unaffected by the presence of A22 (FIG. 7F). Thus, MreB is both qualitatively and quantitatively dispensable for the movement of origin-distal loci, suggesting that it does not participate in this process whatsoever.

Figure 8:
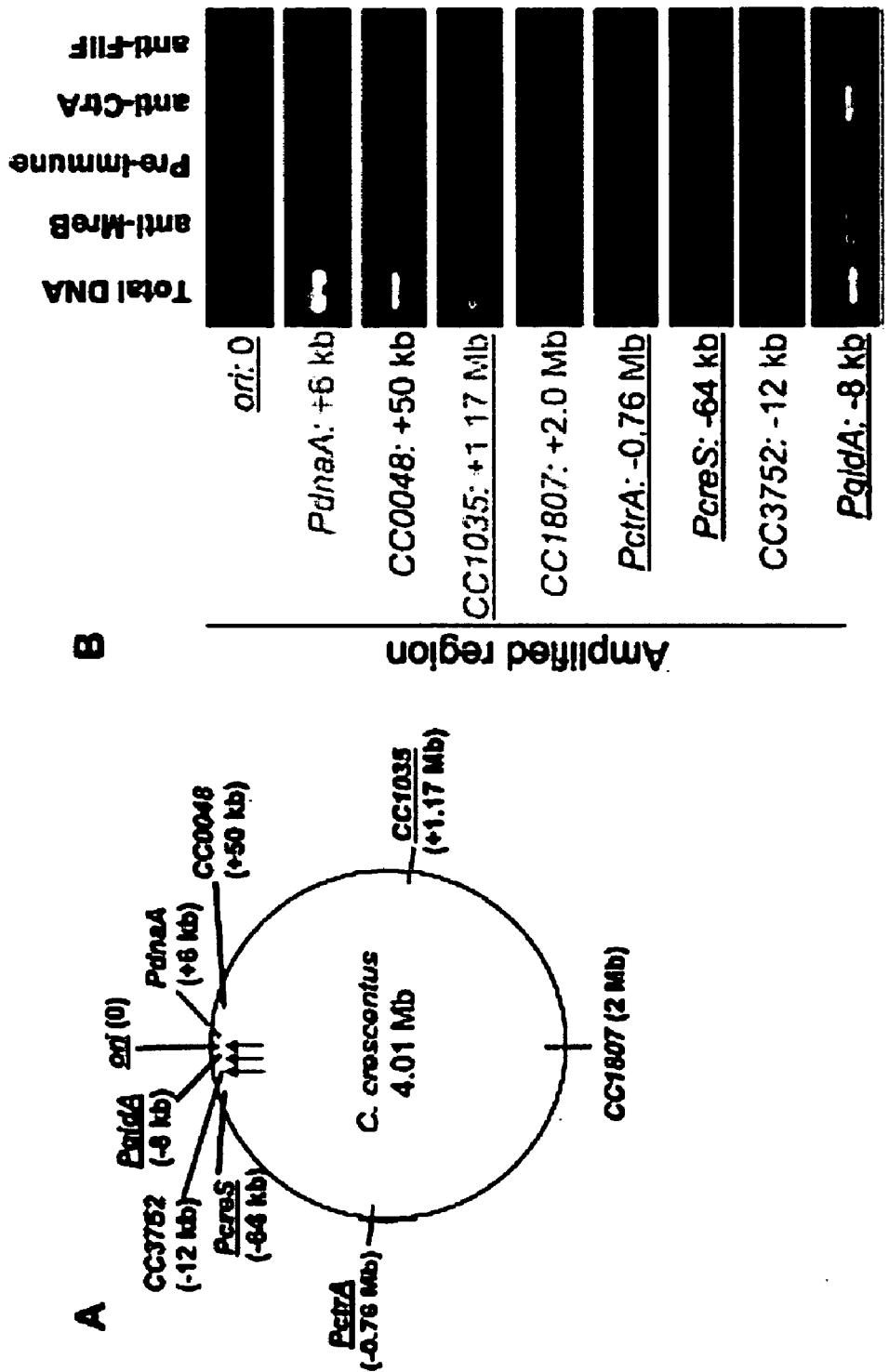
FIG. 8. MreB Binds a Specific Chromosomal Region near the Origin ChIPs were performed using anti-MreB, MreB preimmune, anti-CtrA, and anti-FliF antisera. The origin, PdnaA, CC0048, CC1035, CC1807, PctrA, PcreS, CC3752, and PgidA chromosomal loci were then PCR amplified. (A) Schematic of the genetic positions of the amplified loci. The underlined loci are known CtrA binding targets. Red arrows point to loci that bind MreB. (B) Ethidium bromide-stained agarose gel electrophoresis of the PCR reactions for each amplified locus from each ChIP. The distance of each locus is shown, color coded to correspond to the schematic in (A).

MreB Associates with Origin-Proximal Loci. The specific inhibition of origin movement by A22 raises the possibility that the duplicated origin moves to the opposite pole through a specific physical association with MreB, much as eukaryotic centromeres are segregated by association with microtubules. We sought to detect such an association in vivo by chromatin immunoprecipitation (ChIP). Following previously established protocols, *Caulobacter* extracts were ChIP'ed with polyclonal antisera raised against purified *Caulobacter* MreB. PCR was then used to amplify specific segments of the *Caulobacter* chromosome. In multiple independent experiments, the origin of replication, the gidA promoter region (8 kb to the left of the origin), and the CC3752 gene (12 kb to the left of the origin) robustly amplified, indicating that they biochemically associate with MreB (FIG. 8). We detected a faint signal with primers to the dnaA promoter located 6 kb to the right of the origin (FIG. 8), possibly reflecting the fact that dnaA is at the edge of the MreB binding region. When regions farther from the origin (64 kb, 760 kb, and 2 Mb to the left and 50 kb and 1.17 Mb to the right) were amplified from the MreB ChIPs, no signal was detected (FIG. 8), indicating that MreB does not associate with these sites and that the association of MreB with the chromosome exhibits specificity. The origin coimmunoprecipitation with MreB was significantly reduced, though not abolished, in the presence of A22.

As a control, we performed ChIP experiments with an anti-CtrA antibody. CtrA is a DNA binding response regulator whose binding sites throughout the genome have been systematically characterized, such that we know the identities both of loci that bind CtrA as well as those that do not bind CtrA. In multiple independent experiments, five known CtrA targets (PctrA, PcreS, PgidA, ori, and PCC1035) were consistently amplified from lysates precipitated with anti-CtrA antibodies, while three loci known to not interact with CtrA (PdnaA, CC1807, CC3752, and PCC0048) never amplified (FIG. 8). Moreover, no loci whatsoever were amplified when the ChIP experiments were repeated with MreB preimmune serum or antibodies to FliF, a flagellar motor known to not bind DNA (FIG. 8).

Thus, the ChIP results indicate that MreB exhibits specificity of interaction with the chromosome and recognizes, at minimum, the origin of replication and sequences 8 kb and 12 kb to the left of the origin. Although these experiments do not differentiate between direct binding of MreB to DNA or to a DNA binding protein complex, MreB's association with an origin-proximal region is consistent with MreB playing a direct role in the movement of the origin region. MreB's lack of association with origin-distal regions also supports our A22 findings, suggesting that MreB directs the movement of the origin region, but that the rest of the chromosome segregates through an MreB-independent mechanism.

DISCUSSION

Eukaryotic cells have long been known to use cytoskeletal proteins for a wide variety of cellular activities including cell shape determination, division, polarization, protein localization, and chromosome segregation. The identification of bacterial cytoskeletal proteins has raised the possibility that these proteins carry out similar functions in bacteria. What is known about the bacterial cytoskeleton is consistent with this notion, with the MreB actin homolog as a particularly attractive candidate for playing a role in chromosome segregation. MreB perturbations lead to defective numbers and positioning of chromosomal loci. However, these defects take several cell cycles to manifest and could be an indirect result of other MreB functions or general cellular deterioration. The dissection of acute activity is required to understand the direct actions of the multifunctional MreB actin. For example, the use of rapidly acting drugs such as cytochalasins and nocodazole has revealed the many roles of actin and tubulin in eukaryotic cells). We thus pursued a pharmacological approach to quickly and specifically perturb MreB and assess its direct involvement in chromosome segregation.

A22 Is a New Tool for Studying MreB Function. A small molecule, A22, discovered in a screen for anucleate *E. coli* cells and shown to convert rod-shaped *E. coli* to round cells mimics MreB depletion and rapidly and reversibly delocalizes MreB in *Caulobacter*. We have shown that seven missense mutations in mreB are each sufficient to render cells completely insensitive to A22, and no mutations in any other genes were found to cause resistance to this drug. Thus, A22 is highly specific for MreB. The combination of A22's high specificity and rapid perturbation of MreB localization make it particularly useful for the temporal analysis of MreB function.

In addition to demonstrating specificity, the A22-resistant mreB alleles shed light on how A22 might interact with MreB. The mutated residues are dispersed throughout the protein, but when mapped onto the crystal structure of a close homolog, they all cluster near MreB's nucleotide binding site. The actin inhibitor latrunculin binds the active site of eukaryotic actin and displaces ATP, preventing monomers from polymerizing, perhaps indicating a parallel with the loss of *Caulobacter* MreB helical polymers upon A22 treatment.

The MreB Actin Directs the Segregation of Origin-Proximal, but Not Origin-Distal Loci. As *Caulobacter* transition from swarmer cells to stalked cells, replication initiates, one of the replicated origins rapidly moves across the cell to the opposite pole, and other loci are sequentially replicated and segregated to their proper cellular destinations. When A22 is added to swarmer cells in which the origin and an origin-distal locus are tagged with fluorescent markers, neither locus separates into discernable foci. Since A22 does not block replication initiation and a full round of replication occurs in the presence of A22, we conclude that these loci are duplicated, but that the replicated loci do not move apart. As a result, the fluorescence foci from each duplicated locus cannot be resolved, causing them to appear as a single dot. MreB thus appears to be essential for *Caulobacter* origin segregation. MreB-depleted *E. coli* cells also segregate their chromosomes in cohesive pairs, suggesting that this may be a general mechanism for bacterial chromosome segregation.

The observation that loci can be replicated without being segregated demonstrates that replication and segregation can be uncoupled. This uncoupling is consistent with the findings from *E. coli* in which migS was identified as a locus responsible for segregation but not replication. In addition, altering the order of chromosomal replication in *E. coli* by debilitating the normal origin and inserting an exogenous origin of replication at another position in the chromosome does not alter the order of chromosomal segregation. This has significant implications for the prevailing "extrusion-capture" model of chromosome segregation. While the force generated by extruding DNA from the replisome may still contribute to chromosome dynamics, it alone is clearly insufficient to drive chromosomes apart, and a replication-independent segregation machinery must exist.

In contrast to the origin, loci in origin-distal regions of the chromosome are able to segregate in the presence of A22, so long as A22 is administered after the origins are replicated and moved to the cell poles. Not only are the origin-distal loci separated in the presence of A22, but A22 has no effect on their cellular position or the kinetics of their movement. These results suggest a two-step mechanism for *Caulobacter* chromosome segregation: first an MreB-dependent polar segregation of the origin region occurs, and then the rest of the chromosome segregates independently of MreB. Since treatment of cells with A22 prior to the movement of the origin to the cell poles blocks the movement of loci throughout the chromosome, it appears that the second step can only occur if the first is completed. This would be consistent with a "harpoon" model for *Caulobacter* chromosome segregation wherein origin movement to its proper location is mediated by MreB, followed by the rest of the chromosome being pulled along behind the origin. The pulling force could come from DNA replication or DNA compaction proteins such as SMC, and the histone-like HU potentially explaining the chromosome partitioning defects observed in these mutants.

A Putative Bacterial Centromere. The A22 experiments demonstrate that the movement of the origin depends on MreB but do not address whether MreB acts on the chromosome itself or acts indirectly by binding to other proteins required for chromosome segregation. ChIP assays demonstrated that MreB biochemically associates either directly or indirectly with chromosomal DNA, and that this association exhibits specificity. The origin and loci −8 and −12 kb away from the origin bound MreB, while sites at −64 kb, +50 kb, and farther from the origin did not. The fact that the origin-proximal region both depends on MreB for segregation and binds MreB suggests that this region could bind to MreB to mediate its segregation, which in turn promotes the segregation of the rest of the chromosome. In this manner, the origin-proximal DNA would function as a bacterial centromere.

At the time of *Caulobacter* origin segregation, MreB is assembled in a spiral that corkscrews along the length of the cell. This MreB spiral could serve as a track for a motor protein to pull one origin to the other pole. Alternatively, the dynamics of MreB monomers within a polarized MreB filament could be harnessed for origin movement.

Understanding the link between MreB and the *Caulobacter* chromosome should prove critical to understanding chromosome segregation. The essential *Caulobacter* ParA and ParB proteins may be candidates for this link: parA and parB mutants exhibit strong chromosome segregation defects, and ParB and MreB bind similar regions of the *Caulobacter* chromosome, slightly to the left of the origin. However, the chromosome segregation defects of the *Caulobacter* par mutants have been largely attributed to their triggering a cell cycle checkpoint, Par protein homologs are not found in *E. coli*, and *B. subtilis* soj (parA) and spo0J (parB) mutants are viable and have very subtle chromosome defects.

In addition to identifying the putative kinetochore complex, many other questions must be addressed, including the role of MreB in chromosome segregation in other bacteria, and the mechanism by which specific loci are delivered to reproducible cellular locations. Our work provides a framework for directing these future studies by demonstrating that MreB physically associates with an origin-proximal region of the chromosome and is required to direct origin segregation, which in turn mediates the movement of the rest of the chromosome.

Experimental Procedures

Bacterial Strains and Growth Conditions. *Caulobacter crescentus* strains CB15N and derivatives were grown in PYE or M2G medium or agar plates supplemented with the appropriate combinations of antibiotics, glucose, xylose, A22, and the A22 diluent, methanol. The FROS strains labeled at both the origin and CC2943, CC3300, CC3656, and CC0091, or singly labeled at CC0786, and CC3192 were generated and characterized in a previous study, where they were referred to as MPO40, MPO53, MPO7, MPO133, MP156, and MP82, respectively. Growth and analysis conditions for the mreB depletion, holB:gfp, and FROS strains have been previously described. The methods for ΦCr30-mediated generalized phage transduction and swarmer cell isolation by Percoll density gradient centrifugation have also been described. Washes were performed by micro centrifugation at 8000 g. Twenty independent A22-resistant *Caulobacter* mutants were isolated by growing 20 single CB15N colonies overnight and plating 109 cells per culture on PYE plates containing 10 μg/ml A22. One A22-resistant colony from each plate was isolated, retested, and characterized. To sequence the mreB gene from these strains, mreB was PCR-amplified and the resulting band was gel-purified (Qiagen) and sequenced. Overlay PCR mutagenesis was used to introduce the T158A point mutation (A509G) into the previously described PxyI: gfp:mreB construct.

Microscopy and Timelapse Imaging. All experiments other than the A22 flow-cell analysis were performed by mounting the samples on 1% agarose pads as described, with the appropriate concentration of A22 added to the agarose. The rates of origin-distal locus segregation were determined by inducing PxyI:lacI:cfp expression with 0.03% xylose for 75 min, isolating swarmer cells, and growing the swarmer cells in M2G liquid medium for 50 min. After 50 min, 10 μg/ml of A22 was added to these liquid cultures, they were mounted onto 1% M2G agarose pads containing 10 μg/ml A22, and a phase and CFP fluorescence image was captured every 2 min for 60 min. The images were analyzed by previously described software to determine the average position and rate of movement of the observed foci.

The A22 flow-cell treatment timelapse images were performed on PxyI:gfp-mreB cells induced for 2 hr with 0.03% xylose. These cells were adhered to polylysine-coated cover slips. The cover slips were then adhered to microscope slides with two parallel strips of double-sided tape (3M), leaving a central channel. An excess of medium containing 0 or 10 μg/ml A22 was pipetted onto one opening of this channel and wicked through by placing a tissue (VWR) on the other end. Images were collected every 30 s.

Analysis of DNA Replication. DNA replication was assessed by incorporation of 32P-labeled dGTP) or chromomycin-stained DNA-content FACS analysis as described previously.

Chromatin Immunoprecipitations. Formaldehyde-crosslinked chromatin immunoprecipitation was performed as described previously. The anti-MreB antibody was raised by cloning the mreB coding sequence into the pET28a vector (Novagen). The resulting His6-tagged MreB was overexpressed in BL21(DE3)/pLysS *E. coli* and purified using Qiagen Ni2+-NTA agarose as described previously. Two milligrams of purified His6-MreB was used to immunize two rabbits (Josman Laboratories, Napa, Calif.). Oligonucleotide primer sequences for the regions PCR amplified are available upon request.

Example 4

An Antibacterial Agent that Targets the Bacterial Actin-Like Protein MreB

Current genetic analyses have identified five genes that are involved in rod shape formation in *E. coli*: pbpA (a structural gene of PBP 2), rodA, mreB, mreC and mreD (Westling-Häggström & Normark 1975; Iwaya et al. 1978; Tamaki et al. 1980; Wachi et al. 1987; Wachi et al. 1988; Wachi et al. 1989; Matsuzawa et al. 1989). Determination of the actin-like structure of MreB has promoted its function as a cytoskeletal protein in rod shape cell formation (Jones et al. 2001; van den Ent et al. 2001). The functions of rodA, mreC and mreD have yet to be determined.

Our aim is to identify molecular targets of A22 and understand the mechanism driving its antibiotic properties. A22 has the potential to function not only as a lead compound in the development of new antibacterial agents, but also as a novel bio-probe for investigating the shape-determination mechanism of *E. coli*. Here we report that a novel MreB mutant was isolated in a genetic screen for resistance to the formation of spherical anucleate cells in response to A22 treatment. Our results lead us to conclude that this bacterial actin-like protein is one target of A22.

TABLE 3

MICs of mecillinam and A22

| Strains | Alleles ponB | mreB | MICs (μg/ml)[a] mecillinam | A22 |
|---|---|---|---|---|
| JE1011 | + | + | 0.25 | 6.25 |
| JST975 | − | + | 0.125 | 3.125 |
| JA221 | − | mreB221 | 0.125 | 100 |
| JSTA221[b] | − | mreB221 | 0.125 | 100 |
| JSTA220[b] | − | + | 0.125 | 3.125 |
| WA221[c] | + | mreB221 | 0.25 | >100 |
| WA220[c] | + | + | 0.25 | 6.25 |
| JM109/pMW218 | + | +/−[d] | 0.125 | 6.25 |
| JM109/pMreB1 | + | +/+[d] | 0.125 | 25 |
| JM109/pMreB221 | + | +/mreB221[d] | 0.125 | 100 |

[a] MICs were determined by a 2-fold serial dilution format as described in the Materials and Methods. The same values were obtained for L agar plates and Mueller Hinton agar plates.
[b] JSTA221 and JSTA220 were constructed by the P1-phage mediated transduction using JA221 zhc-12::Tn10 (mreB221 zhc-12::Tn10) as a donor and JST975 (ponB) as a recipient.
[c] WA221 and WA220 were constructed by the P1-phage mediated transduction using JA221 zhc-12::Tn10 (mreB221 zhc-12::Tn10) as a donor and W3110 (wild-type) as a recipient.
[d] Chromosomal allele/episomal allele are shown.

Results

Isolation of A22-resistant mutant Our strategy for identifying the molecular target(s) of A22 involved isolating resistant mutants which grow in the presence of concentrations of A22 that inhibit growth of the parent strain. After 24 h incubation at 37° C., *E. coli* strains such as JE1011 formed a turbid growth inhibitory zone (φ 12 mm) around a paper disk (φ 8 mm) containing 200 μg of A22. To identify a more suitable parent strain for our selection, we screened for a more drug-sensitive strain that would form clear growth inhibitory zones under similar incubation conditions. JST975 *E. coli*, derived from JE1011, but deficient in penicillin-binding protein 1B (ponB) showed greater A22 sensitivity, forming a clear growth inhibitory zone larger (φ 32 mm) than the parent strain.

Figure 9:
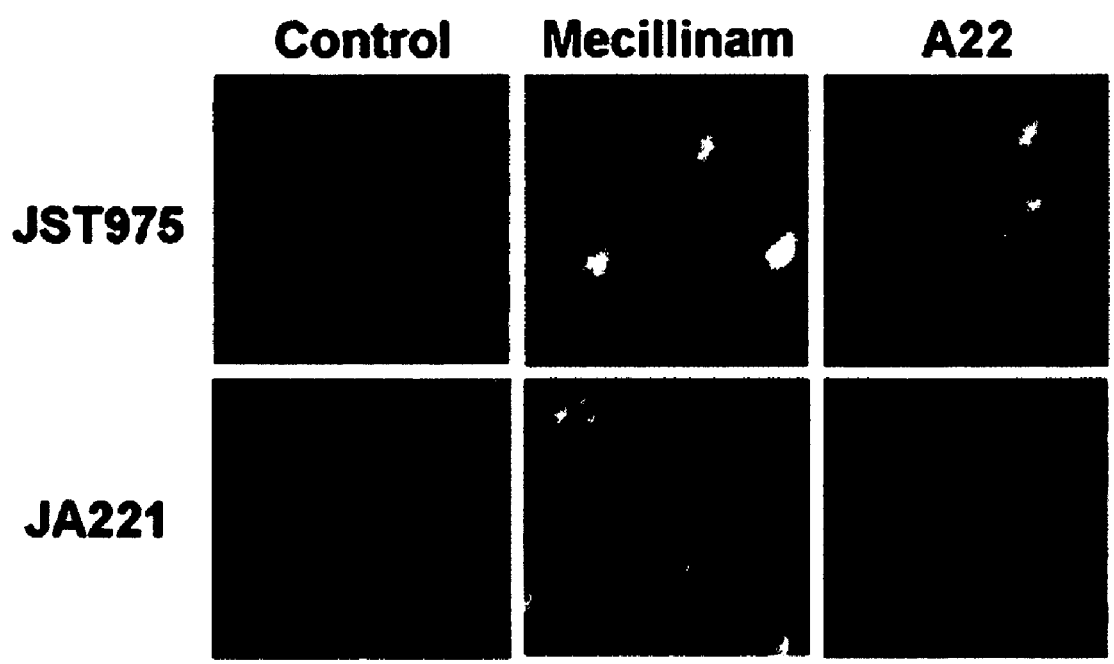
FIG. 9. Effects of A22 and mecillinam on cell shapes of the A22-resistant mutant JA221. Exponentially growing cells of the A22-resistant mutant strain JA221 and the parent strain JST975 were treated with 1 μg/ml mecillinam or 10 μg/ml A22 for 2 h at 37° C. Differential interference contrast microphotographs are shown.

After prolonged (9 days) incubation of the JST975 assay plates, several isolated colonies that grew up within the clear growth inhibitory zones were purified on L plates and their A22-sensitivity was examined. One clone in particular, JA221, was highly resistant to A22, with a minimum inhibitory concentration (MIC) of 100 μg/ml compared to 1.6 μg/ml for JST975 (Table 3). In the presence of 10 μg/ml A22, the resistant mutant JA221 grew as rods while the parent strain JST975 formed spherical cells, as reported previously for ponB+ strains (FIG. 9) (Iwai et al. 2002). The A22-resistant mutant JA221 was sensitive to mecillinam (Table 3) and formed spherical cells upon mecillinam treatment (FIG. 9), indicating that PBP 2 functioned normally in the mutant cells. The infrequent appearance of anucleate JA221 cells suggests that chromosome segregation was normal.

Mapping the mutation that confers A22 resistance Since A22 results in the formation of spherical *E. coli* cells, it is likely to interfere with rod-shape-determining proteins of *E. coli*. Mutations in five genes, pbpA, rodA, mreB, mreC and mreD, are known to result in spherical cell formation. The pbpA/rodA operon is located at 14 min on the *E. coli* genetic map. Genes mreB, mreC and mreD, located at 71 min, also are likely to form an operon.

We used P1-phage-mediated transduction mapping to test whether A22-resistant JA221 carried a mutation in one of these genes. The transposon marker zhc-12::Tn10, located at 71 min, is co-transducible with the mreB129 mutation with a frequency of 66%. Following P1-phage mediated transduction of zhc-12::Tn10 into JA221, we obtained A22-sensitive transductants with a frequency of 67%. A22-resistance was transferable from an A22-resistant transductant (A22$^r$ zhc-12::Tn10) into the parent strain JST975, as well as into the wild-type stain W3110 with similar frequencies (Table 3). No linkage was observed between A22-resistance and a transposon marker zbd-601::Tn10, located at 14 min, which is co-transducible with pbpA at a frequency of 45%. These mapping results indicate that the A22-resistant mutation is located at approximately 71 min. Furthermore, we found A22 resistance to be conferred solely by the mutation at 71 min in JA221, and independent of any mutation in ponB.

Figure 10:
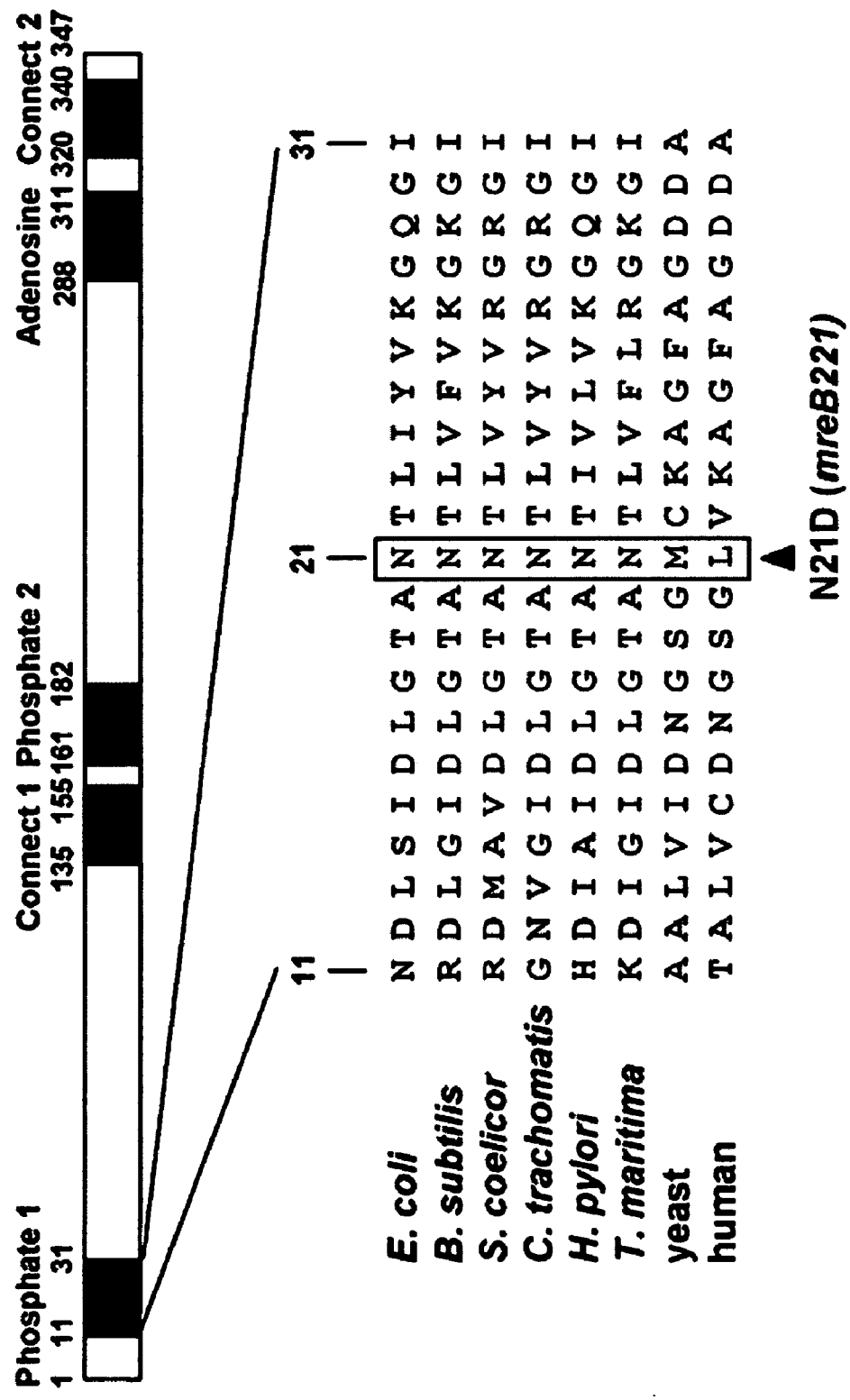
FIG. 10. Site of the A22-resistant mreB221 mutation within a schematic representation of the conserved domains of the bacterial actin-like protein MreB. The conserved domains (Phosphate 1, Phosphate 2, Connect 1, Connect 2, and Adenosine) are colored. Numbers represent amino acid residue numbers of the *E. coli* MreB protein. Amino acid sequences of the Phosphate 1 domains of bacterial MreB homologues that align with eukaryotic actins from yeast and human are highlighted. Sequences are MreB homologues from *Escherichia coli* (*E. coli*), *Bacillus subtilis* (*B. subtilis*), *Streptomyces coelicor* (*S. coelicor*), *Chlymadia trachomatis* (*C. trachomatis*), *Helicobacter pylori* (*H. pylori*), *Thermotoga maritima* (*T. maritima*), and *Schizosaccharomyces pombe* Act1 (yeast), and human ActS (human). N21D indicates the substitution of Asn21 to Asp in the A22-resistant mreB221 mutation.

Identification of the A22-resistant mutation P1-phage-mediated transduction mapping suggested strongly that JA221 A22-resistance results from a mutation in either mreB, mreC or mreD. We used PCR to amplify this region of the JA221 chromosomal DNA, which was ligated into a plasmid and transformed into *E. coli*. The sequences of three independently isolated clones were compared with that of the wild-type clone. A G to A transition in the mreB gene, resulting in substitution of Asn21 to Asp of the MreB protein, was the only mutation found in all three isolates (FIG. 10). It is notable that *E. coli* strains generated for DNA sequence analysis, such as JM109/pMreB221, which express the wild-type chromosomal mreB as well as the JA221 mutant allele on the plasmid, showed increased resistance to A22 (Table 3). Thus we conclude that this substitution mutation is responsible for A22-resistance, and that it is dominant to the wild-type allele with regard to A22-sensitivity. The mutant allele, named mreB221, complemented both the mecillinam-resistance and spherical shape phenotypes of mreB129, indicating that the mutant MreB221 protein retains its role in rod-shaped cell formation in *E. coli*.

Figure 11:
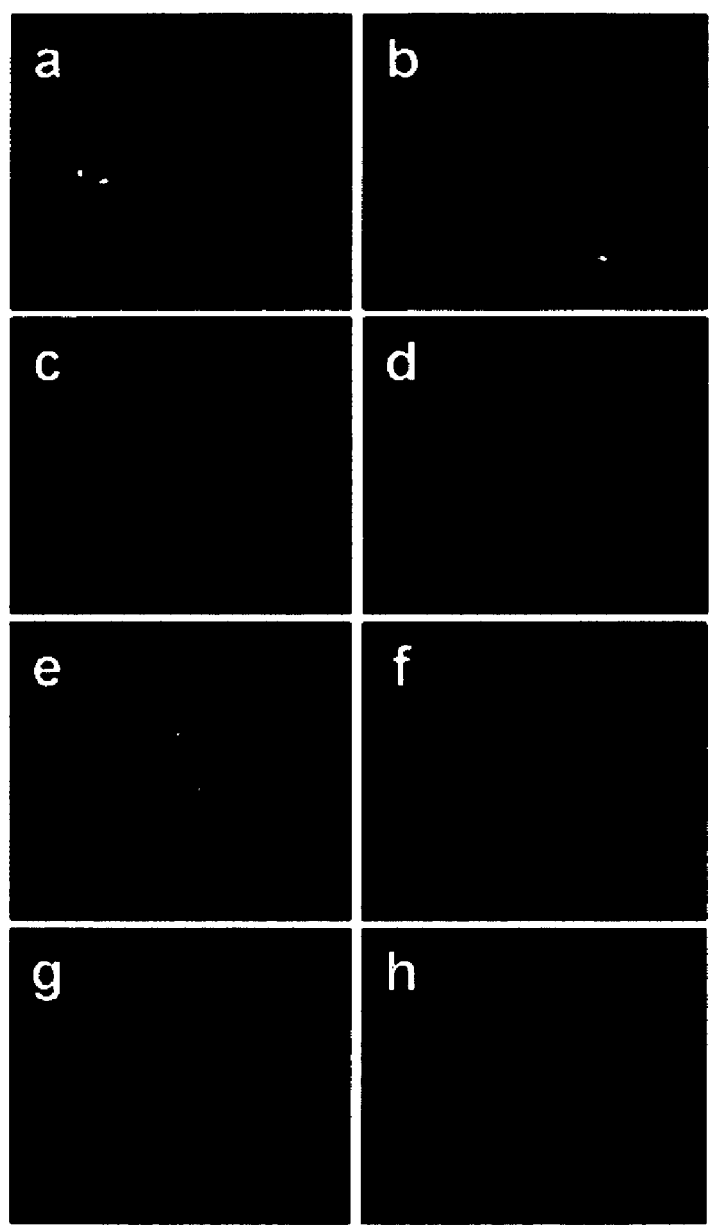
FIG. 11. In vivo effects of A22. Exponentially growing JM109/pMreB1-GFP cells were treated with 10 μg/ml of A22, and changes in cell shape and GFP fluorescence were observed. (a, b) no treatment; (c, d) 30 min after A22 treatment; (e, f) 60 min after A22 treatment; (g, h) 120 min after A22 treatment.

Effect of A22 on the MreB helical structures in vivo The results of the genetic analysis demonstrated above strongly suggest that the target molecule of A22 is the MreB protein. It was recently shown that the MreB forms helical structures in *E. coli* as well as *B. subtilis*. In JM109 cells expressing an MreB-GFP fusion protein, cells viewed by fluorescence microscopy exhibited the regularly spaced dots and transverse bands typical of MreB helical structures (FIGS. 11a and 11b). Following a 30-minute treatment with 10 μg/ml A22, these cells broadened and fluorescent dots and bands disappeared (FIGS. 11c and 11d), suggesting that A22 disrupts MreB helical structures. Cells rounded further after 60 minutes (FIGS. 11e and 11f), and were almost spherical after 120 minutes (FIGS. 11g and 11h). In rounded cells, MreB-GFP appeared as discrete dots located close to the cell surface (FIGS. 11e-11h), which may be the result of aggregation of MreB-GFP protein de-polymerized by A22.

Essentiality of the mreB gene for *E. coli* cell growth We reported previously on the isolation of a mecillinam-resistant Δmre678 mutant strain in which approximately 7-kb of the genomic DNA including the mreB, mreC and mreD genes, the hypothetical open reading frame orfE (yhdE) and the mg gene encoding RNase G, are deleted. Since a point mutation in MreB suppresses A22-induced lethality, we postulate that the wild-type mreB gene product is the target of A22. We hypothesize that the mreB gene is also essential in *E. coli*, as reported for *Salmonella thypimurium* and *B. subtilis*. If so, growth of the Δmre678 mutant strain must be associated with an unidentified second-site suppressor mutation. To test the phenotype of the Δmre678 mutation in the absence of this suppressor, the Δmre678 mutation was transduced into wild-type cells in the absence or presence of various combinations of plasmid-bourne mreB, mreC or mreD genes. As shown in Table 4, only cells carrying all three mre genes—B, C and D (supplied in trans from the plasmids)—yielded viable transductants (Table 4). These results indicate that mreB, along with mreC and mreD, are essential for *E. coli* cell growth, and that the MreB protein can serve as a lethal target of antibacterial agents.

TABLE 4

Essentiality of the mreB, mreC and mreD genes in the wild-type *E. coli* cells

| Plasmids | Genes supplied in trans | Δmre678/Tc$^r$ (%)$^{a)}$ |
|---|---|---|
| — | — | 0/20 (0) |
| pMEL8 | mreB, mreC, mreD | 12/20 (60) |
| pMEL7 | mreB, mreC | 0/20 (0) |
| pMEL6 | mreB | 0/20 (0) |
| pMEG1 | mreC, mreD | 0/20 (0) |
| pMEL6, pMEG2 | mreB, mreD | 0/20 (0) |

$^{a)}$P1-phage mediated transduction was carried out using AT1325-678 zhc-12::Tn10 (Δmre678 zhc-12::Tn10) as a donor and MG1655 (wild-type) carrying plasmid(s) shown in the first column as a recipient. The right-hand column indicates the number of transductants carrying the Δmre678 mutation (Δmre678)/the number of tetracycline-resistant transductants (Tc$^r$).

Docking study The location of the mreB mutation identified in our screen suggests strongly that A22 binds to the ATP-binding pocket of MreB. Using the coordinates of the 3D structure for *Thermotoga maritima* MreB protein (van den Ent et al. 2001; FIG. 5A), we conducted an in silico docking study of A22. Our models suggest that A22 is likely to associate with the ATP-binding pocket, and thus could block access to ATP (FIG. 5B). In *T. maritima* MreB, asparagine residue 14 occupies a position analogous to Asn21 in *E. coli* MreB at the edge of the ATP-binding pocket; hence the Asn to Asp substitution in mreB221 may prevent access of A22 to the ATP-binding pocket.

To overcome multi-drug-resistant strains of bacteria, new antibacterial agents directed at novel molecular targets must be developed for the chemotherapeutic treatment of bacterial infectious diseases. In a screen for inhibitors of chromosome partitioning, we found a novel S-benzylisothiourea derivative, S-(3,4-dichlorobenzyl)isothiourea or A22, which induces spherical cells and spherical anucleate cells in *E. coli*. Here we describe the isolation, mapping and molecular identification of an A22-resistant mutant which proves to be one molecular target of A22. A transition mutation in the mreB gene that encodes a single amino acid substitution in the bacterial actin-like protein MreB confers A22 resistance. The mutant allele mreB221 was dominant over the wild-type allele (Table 3). Fluorescence microscopy images of MreB in vivo demonstrated that after 30 min of A22 treatment, MreB-mediated helical structures disappeared (FIGS. 11*c* and 11*d*). These results strongly suggest that the MreB protein is a target of A22, and if so, that the MreB protein should be essential for *E. coli* cell growth. Using P1-phage mediated transduction of Δmre678 mutation into a wild-type strain in which plasmid-mediated expression of mre gene products is present or absent, we demonstrated that mreB, mreC and mreD are essential for the growth of *E. coli* (Table 4). These results indicate that the MreB protein can be a lethal target of antibacterial agents.

Figure 12:
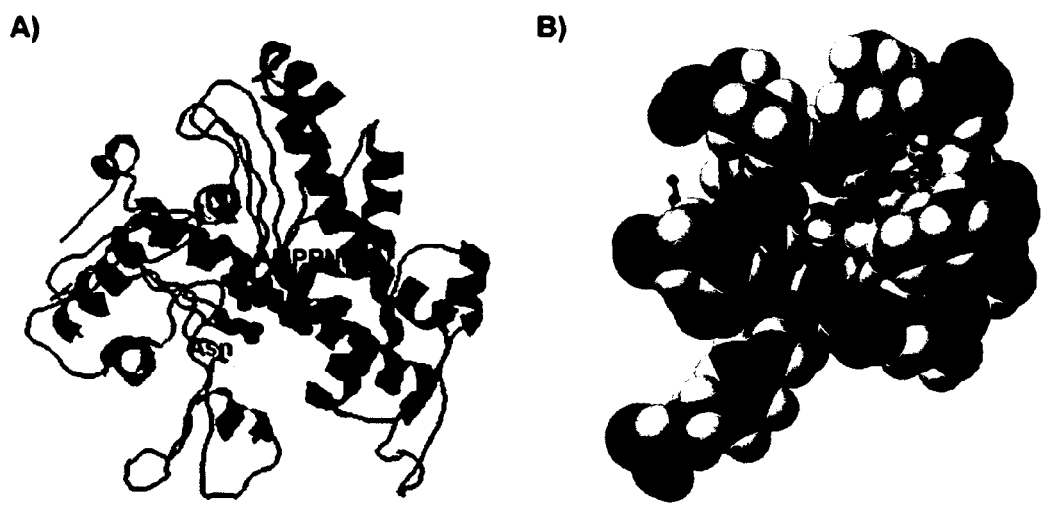
FIG. 12. The 3D structures of the *T. maritima* MreB protein (PDB code; 1JCG) and the docking study of MreB with A22. (A) *T. maritima* MreB drawn by using the RasMol program (Sayle & Milner-White 1995). Asparagine 14 and the ATP analogue, AMPPNP, are shown in red. (B) A model for A22 docking to *T. maritima* MreB. The docking study was performed using a docking software BioMedCAChe active site as described in the Experimental procedures. Amino acid residues located within 4 Å of AMPPNP (Ala13, Asn14, Arg63, Gly155, Gly156, Gly179, Asp180, Met182, Glu204, Lys207, Ile208, Gly286, Gly287, Leu289 and Leu312) are shown in the space filling model (carbon atoms, gray; oxygen atoms, red; nitrogen atoms, blue; sulfur atoms, yellow; hydrogen atoms; white). Asn14 is labeled. AMPPNP and A22 (overlaid) are depicted by ball and cylinder models (AMPPNP, cyan; A22, magenta).

The A22-resistant MreB221 protein has an amino acid substitution of Asn21 (*E. coli*'s numbering) to Asp (FIG. 10). Crystallographic studies of MreB, purified from the thermophilic bacterium *T. maritima*, showed that the position occupied by this residue, which corresponds to Asn14 of *T. maritima* MreB, is involved in hydrogen bond formation with β-phosphate of ATP. Although A22 is structurally dissimilar to ATP, the position of the MreB221 mutation suggests that A22 competes with ATP by binding within the MreB ATP-binding pocket. This hypothesis is further supported by in silico modeling of A22 interactions with MreB (FIG. 12B). Substitution of Asn14 (*T. maritima*'s numbering) to Asp may not diminish ATP-binding to MreB, because this interaction is mediated by the amide groups of the Ala13-Asn14 dipeptide backbone, and not the side chain of Asn14. This may explain why JA221 mutants expressing MreB221 protein maintain rod-shaped cells.

It is notable that the residue at the position of *E. coli* MreB Asn21 is highly conserved as asparagine among many bacterial MreB homologues (FIG. 3). Furthermore, structurally-related eukaryotic actins do not maintain Asn at the equivalent position. Therefore, A22 could function as a lead compound in the development of selective drugs targeting bacterial MreB homologues.

Recent reports demonstrate that the mreB gene, originally discovered as a rod-shape-determining gene in a study of mecillinam-resistant mutants, encodes a structural and functional homologue of eukaryotic cytoskeletal actin. This role of MreB in cell morphogenesis is easily imagined, since mutants form spherical cells, and inhibition of MreB by A22 also induces spherical cell formation in *E. coli*. Several investigators have recently suggested an additional role for this protein, and its homologues, in chromosome segregation. The identification of A22 in a screen for inhibitors of chromosome segregation provides further evidence for this function of MreB. In fact, anucleate cells were frequently observed in cultures treated with A22. Since mreB is essential for cell growth, further analysis of the role of MreB in chromosome segregation presents some challenges. We expect A22 to be a powerful tool in future studies of MreB function.

A22 does not lyse wild-type *E. coli* cells, and as such, the A22-mediated growth inhibitory zone with these cells appears turbid. To facilitate the isolation of A22-resistant mutants a PBP 1B-defective (ponB$^-$) mutant strain, JST975, which forms a clear growth inhibitory zone upon A22 treatment, was selected as the parent strain in our screen. In a liquid culture of A22-treated JST975, ghost-like cells were frequently observed among spherical cells, indicating that A22 induces cell lysis in the absence of PBP 1B. This correlates well with the increased sensitivity of mreB mutant strains to β-lactam antibiotics. In future screens for antibacterial agents derived from A22, it will be important to consider that the antibacterial effect of A22 on wild-type *E. coli* cells may be enhanced by simultaneous treatment with sub-lethal concentrations of β-lactam antibiotics.

Although A22 is not sufficiently potent to be considered as an antibiotic in its present form, it may serve well as a lead compound for chemical modification to develop novel antibacterial agents. A structure-activity relationship study suggested that dichloro-substitution on the S-benzyl group may enhance activity. One strategy to optimize MreB inhibitors may involve identification of the atomic interactions between MreB and an inhibitor in an MreB:inhibitor co-crystal.

Almost all widely-used antibiotics and synthetic antibacterial compounds target biosynthetic pathways such as DNA synthesis (i.e. quinolones), RNA synthesis (i.e. rifampicins), protein synthesis (i.e. aminoglycosides, tetracyclines and chloramphenicols) and cell wall peptidoglycan synthesis (i.e. β-lactams and vancomycin) (for a review, Walsh 2003). Linezolid, the most recently introduced antibiotic, inhibits protein synthesis. Since no antibacterial agents targeting bacterial cytoskeletal proteins have been developed as yet, resistant pathogens have yet to evolve. We expect A22 to function as a lead compound for the development of new antibacterial agents effective against multi-drug resistant pathogens. We propose that A22 and the related compounds that act on the bacterial actin-like protein MreB be named "bactinin", for "bacterial actin inhibitor".

Experimental Procedures

Bacterial strains used E. coli K-12 strains JE1011 (F$^-$ leuB thr trp his thy ara lac xyl mtl rpsL tonA), JST975 (the same as JE1011 but ponB) (Tamaki et al. 1977), W3110 (wild-type), MG1655 (wild-type), DV14 (F$^-$ metB1 panD2 panF1 zhc-12::Tn10) (Vallari & Rock 1985), CAG12149 (F$^-$ zbd-601::Tn10) (Singer et al. 1989), AT1325-678 (F$^-$ lip-9 thi-1 his-4 purB15 proA2 mtl-1 Δmre678) (Wachi et al. 1987) and JM109 [recA1 endA1 gyrA96 thi-1 hsdR17 Δ(lac-proAB) supE44 relA1 F' (traD36 proAB$^+$ lacI$^q$ lacZΔM15)] (Yanisch-Perron et al. 1985) were used in this study. Cells were grown in Lennox (L) medium (1% Bactopeptone, 0.5% yeast extracts, 0.5% NaCl, 0.1% glucose, pH 7.2, supplemented with 20 µg/ml thymine). For the growth of AT1325-678, 0.1 µg/ml lipoic acid was supplemented. The A22-resistant mutant JA221 arose from JST975 (ponB$^-$) by spontaneous mutagenesis: JST975 cells grown in L medium were inoculated at $10^5$ cells/ml into 50° C. molten L agar medium and solidified in plastic plates. Plates were incubated for 24 h at 37° C. following placement of a paper disk (φ8 mm) soaked with 20 µL of A22 solution (10 mg/ml in methanol) at each center. A clear growth inhibitory zone of φ 32 mm formed around each paper disk. Several colonies grew within the inhibitory zone after 9 days incubation, and these were purified on L agar plates and their A22-sensitivity tested. Among them, one A22-resistant clone, designated JA221, was investigated.

Determination of MIC Minimal inhibitory concentrations (MICs) were determined using a standard 2-fold serial dilution format on L agar plates. Ten microliters of stationary culture diluted in 0.85% NaCl to $10^6$ cells/ml were spotted on per plate. Following incubation at 37° C. for 24 h, the MIC was defined to be the lowest concentration that resulted in greater than 99.9% inhibition of colony formation. MICs were also determined on Mueller Hinton agar plates (0.2% beef extract, 1.75% acid digest of casein, 0.15% soluble starch, 1.5% agar, pH 7.3).

Identification of the mutation point The mreB locus in JST975 and JA221 was amplified by PCR with primers (SEQ ID NO:1) 5'-ATGGGAGTGTGCTTGTCGACTCGCC-3' and (SEQ ID NO:2) 5'-ACCAGGCAGGGTCGACAGA-CACTTC-3'. The resulting 1.3-kb DNA fragments were digested with Sal I and subsequently cloned into the SalI site of pMW218 (Takara Bio Inc., Ohtsu, Japan). Three independently-isolated clones from JST975 and JA221, respectively, were sequenced by the dideoxy method using an automated fluorescence DNA sequencer (Long-Read Tower, Amersham Bioscience, NJ, USA) and the Thermo Sequenase Dye Terminator (Cy5.5 and Cy5) sequencing kit (Amersham Bioscience). The region encoding mreC and mreD from JST975 and JA221 was sequenced similarly using primers (SEQ ID NO:3) 5'-GGAGAACCGGMGCTTAATACAGAG-3' and (SEQ ID NO:4) 5'-TTTAGCATGCCTGGTCTGATACGAG-3'.

Construction of a mreB-gfp fusion plasmid A DNA fragment encoding the wild-type mreB gene was PCR-amplified from pMreB1 with primers (SEQ ID NO:5) 5'-ATGGGAGT-GTGCTTCTAGACTCGCC-3' and (SEQ ID NO:6) 5'-TGC-CTGCATCGCTAGCCTCTTCGCT-3'. After cutting with Xba I and Nhe I, the PCR-generated DNA fragments were ligated to an XbaI-NheI-cut gfp vector pQIB-T7-GFP (Qbiogene Inc., Irvine, Calif., USA), resulting in an mreB-gfp translational fusion. From the resulting plasmid, an Aor51HI-HindIII fragment encoding the C-terminal portion of MreB fused with GFP was isolated and used to replace the Aor51HI-HindIII fragment of pMreB1, resulting in a plasmid pMreB1-GFP that expresses the MreB-GFP fusion protein from the native mreB promoter. Fluorescent microscope (Axioskop 2, Carl Zeiss Co. Ltd., Oberkochen, Germany) images were obtained using a chilled 3CCD camera (MicroMax, Roper Industries Inc., Bogart, Ga., USA).

Docking study Computational modeling of the atomic interactions between A22 and MreB was accomplished in the docking program BioMedCAChe active site (Fujitsu, Kawasaki, Japan) using the coordinates of the *T. maritima* MreB 3D structure (PDB code; 1JCG). The protein structure was optimized using PM5 semi-empirical calculations. The settings for the genetic algorithm runs were kept at their default values: population size 50, crossover rate 0.8, elitism 7, maximum generations 3,000, mutation rate 0.3 and convergence 1.0 kcal. In the final docking runs, the amino acids residues located within 4 Å of the AMPPNP ligand were defined.

Determination of the essentiality of the mreB gene E. coli wild-type strain MG1655 was transformed with all possible combinations of plasmid(s) encoding mreB, mreC and mreD. Plasmids used were pMEL8 (mreB mreC mreD), pMEL7 (mreB mreC), pMEL6 (mreB), pMEG1 (mreC mreD) and pMEG2 (mreD) (Wachi et al. 1987; Wachi et al. 1988; Wachi et al. 1989). Transcription of the mreC and/or mreD genes on pMEG1 or pMEG2 was under control of the lacUV5 promoter. Tetracycline-resistant transformants were selected from P1 phage-mediated transduction of plasmid-containing MG1655 (wild-type) recipients with AT1325-678 zhc-12::Tn10 (Δmre678 xhc-12::Tn10) (Wachi et al. 1987 and this study) donors. Presence or absence of the Δmre678 mutation in the transformants was determined by PCR-amplification of the non-essential mg region deleted in the Δmre678 E. coli mutation (Wachi et al. 1997; Wachi et al. 1999), using primers, (SEQ ID NO:7) 5'-GGAGAAACCGCGCGACGCA-GAGCATGCGG-3' and (SEQ ID NO:8) 5'-GGCTTCTAC-CGCATGCCAGTCGCGGATT-3'.

Synthesis of A22 Thiourea was suspended in dehydrated ethanol, and 3,4-dichlorobenzyl chloride was added to the suspension. The mixture was heated at 130° C. to reflux for several hours and then cooled to room temperature. The reaction mixture was concentrated under vacuum, and the resulting residue was diluted with methanol. The product was purified by re-crystallization from diethyl ether. The structure of the compound was confirmed by $^1$H-NMR spectrometry. Thiourea was purchased from Sigma-Aldrich Co. (St. Louis, Mo., USA) and 3,4-dichlorobenzyl chloride from Tokyo Kasei Kogyo Co., Ltd. (Tokyo, Japan).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An antibiotic formulation comprising the structure:

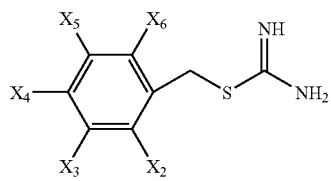

where $X_2$ and $X_4$ are Cl; $X_3$ and $X_6$ are H; and $X_5$ is selected from F, Br, I, a lower alkyl, $CF_3$, $CCl_3$, $NO_2$, $SO_2$, $-OCH_3$, and SH; wherein said compound has a minimum inhibitory concentration against *E. coli* of less than 5 μg/ml.

* * * * *